United States Patent
Reems et al.

(10) Patent No.: US 10,555,973 B2
(45) Date of Patent: Feb. 11, 2020

(54) THERAPEUTIC COMPOSITIONS

(71) Applicant: University of Utah Research Foundation, Salt Lake City, UT (US)

(72) Inventors: Jo-Anna Reems, Salt Lake City, UT (US); Jan Pierce, Sandy, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 30 days.

(21) Appl. No.: 15/450,566

(22) Filed: Mar. 6, 2017

(65) Prior Publication Data
US 2018/0250343 A1    Sep. 6, 2018

(51) Int. Cl.
| | |
|---|---|
| *A61K 9/50* | (2006.01) |
| *A61K 35/50* | (2015.01) |
| *A61K 38/17* | (2006.01) |
| *A61K 31/728* | (2006.01) |
| *A61K 45/06* | (2006.01) |
| *A61K 35/28* | (2015.01) |
| *A61L 27/36* | (2006.01) |
| *A61L 27/26* | (2006.01) |
| *A61L 27/20* | (2006.01) |
| *A61L 27/22* | (2006.01) |
| *A61L 27/54* | (2006.01) |
| *A61L 24/04* | (2006.01) |
| *A61L 24/08* | (2006.01) |
| *A61L 24/10* | (2006.01) |
| *A61L 24/00* | (2006.01) |
| *A61K 38/18* | (2006.01) |
| *A61K 9/00* | (2006.01) |
| *B01D 21/26* | (2006.01) |
| *A61K 9/19* | (2006.01) |

(52) U.S. Cl.
CPC ............ *A61K 35/50* (2013.01); *A61K 9/0014* (2013.01); *A61K 31/728* (2013.01); *A61K 35/28* (2013.01); *A61K 38/1709* (2013.01); *A61K 38/1808* (2013.01); *A61K 45/06* (2013.01); *A61L 24/0005* (2013.01); *A61L 24/0015* (2013.01); *A61L 24/043* (2013.01); *A61L 24/08* (2013.01); *A61L 24/10* (2013.01); *A61L 27/20* (2013.01); *A61L 27/22* (2013.01); *A61L 27/26* (2013.01); *A61L 27/3604* (2013.01); *A61L 27/365* (2013.01); *A61L 27/54* (2013.01); *B01D 21/26* (2013.01); *A61K 9/0019* (2013.01); *A61K 9/19* (2013.01); *A61L 2400/06* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 8,709,494 | B2 | 4/2014 | Daniel |
| 9,132,156 | B1 | 9/2015 | Werber et al. |
| 9,814,746 | B2 | 11/2017 | Werber et al. |
| 2014/0050788 | A1 | 2/2014 | Daniel et al. |
| 2014/0336600 | A1* | 11/2014 | Harrell ................ C12N 5/0605 604/319 |
| 2015/0025366 | A1* | 1/2015 | Harrell ............... A61B 10/0048 600/424 |

OTHER PUBLICATIONS

Gotsch et al. The Journal of Maternal-Fetal & Neonatal Medicine, 21:8, 529-547, 2009 (Year: 2009).*
Vaisbuch et al. (Am J Obstet Gynecol 2008;199:426.e1-426.e7.) (Year: 2008).*
Tisi et al. (J Nutr. Jul. 2004;134(7):1754-8.) (Year: 2004).*
Hoath et al. (International Journal of Cosmetic Science, 2006, 28, 319-333) (Year: 2006).*
Davydova et al. Acta Naturae. Jul. 2009; 1(2): 98-103. (Year: 2009).*
Vogt et al. (Chapter 1: Biology of the Hair Follicle. In. Hair Growth and Disorders. Blume-Peytavi et al. Eds. Springer-Verlag Berlin Heidelberg: 2008; pp. 6-7) (Year: 2008).*
Amnio Technology LLC; "PalinGen® InovōFlo™"; Amnio Technology; [retrieved on Apr. 6, 2018]; 4 pages; Retrieved from <URL: https://amniotechnology.com/products/palingen-inovoflo/ >.
MimMedx Group Inc.; "MiMedx®"; AmnioFix; [retrieved on Apr. 6, 2018]; 4 pages; Retrieved from <URL: http://mimedx.com/ >.
Pierce et al.; "Collection and Characterization of Amniotic Fluid from Scheduled C-Section Deliveries"; Cell and Tissue Banking; (Sep. 2016); pp. 413-425; vol. 17, Issue 3; <doi: 10.1007/s10561-016-9572-7 >.
Underwood et al.; "State of the Art—Amniotic Fluid: Not Just Fetal Urine Anymore"; Journal of Perinatology; (2005); pp. 341-348; vol. 25; <doi: 10.1038/sj.jp.7211290 >.

* cited by examiner

Primary Examiner — Susan T Tran
(74) Attorney, Agent, or Firm — Thorpe North & Western, LLP; David W. Osbourne

(57) ABSTRACT

A therapeutic composition can include an amount of amniotic fluid having a therapeutically effective amount of at least one protein, hyaluronic acid, or both. The therapeutic composition can be substantially free of lanugo, vernix, and cells harvested with the amniotic fluid.

28 Claims, 19 Drawing Sheets

| | |
|---|---|
| 0.0 | Values below the Limit of Detection (LOD) |
| 1,585.6 | Value above the highest standards |

| Amniotic Fluid #1 | | Amniotic Fluid #2 | | Amniotic Fluid #3 | |
|---|---|---|---|---|---|
| | | | | 2B4 | 12.4 |
| 4-1BB | 9.3 | 4-1BB | 10.3 | 4-1BB | 17.6 |
| 6Ckine | 1,951.1 | 6Ckine | 853.0 | 6Ckine | 4,306.1 |
| A2M | 12,479.0 | A2M | 1,467.20 | A2M | 6,045.0 |
| ACE-2 | 11,918.9 | ACE-2 | 7,202.7 | ACE-2 | 3,907.4 |
| Activin A | 525.3 | Activin A | 331.9 | Activin A | 454.4 |
| ADAM-9 | 683.8 | ADAM-9 | 1,059.9 | ADAM-9 | 678.0 |
| Adiponectin | 14,931.2 | Adiponectin | 18,515.7 | Adiponectin | 23,267.0 |
| Adipsin | 5,044.0 | Adipsin | 4,716.1 | Adipsin | 7,967.0 |
| aFGF | 16.6 | | | aFGF | 31.1 |
| AFP | 18,578.2 | AFP | 9,886.0 | AFP | 11,377.3 |
| AgRP | 9.2 | AgRP | 11.3 | AgRP | 15.3 |
| Albumin | 45,883.5 | Albumin | 28,303.1 | Albumin | 35,966.5 |
| ALCAM | 642.8 | ALCAM | 660.6 | ALCAM | 1,161.1 |
| AMICA | 454.5 | AMICA | 165.5 | AMICA | 466.8 |
| ANG | 1,085.1 | ANG | 1,006.2 | ANG | 1,043.4 |
| ANG-1 | 1,205.3 | ANG-1 | 2,752.2 | ANG-1 | 2,955.6 |
| ANG-2 | 148.9 | ANG-2 | 56.1 | ANG-2 | 721.1 |
| ANG-4 | 446.0 | ANG-4 | 174.6 | ANG-4 | 114.9 |
| Angiostatin | 1,105.4 | Angiostatin | 926.0 | Angiostatin | 943.6 |
| ANGPTL4 | 30,891.8 | ANGPTL4 | 30,572.7 | ANGPTL4 | 37,559.5 |
| ApoA1 | 412.1 | ApoA1 | 107,816.8 | ApoA1 | 89,947.5 |
| ApoC1 | 815.3 | ApoC1 | 1,714.3 | ApoC1 | 4,697.2 |
| ApoC2 | 232.0 | ApoC2 | 1,887.2 | ApoC2 | 16,720.1 |
| ApoC3 | 177.6 | ApoC3 | 494.9 | ApoC3 | 755.3 |
| ApoE | 216.2 | ApoE | 3,417.6 | ApoE | 5,804.8 |
| ApoH | 25,828.3 | ApoH | 18,078.0 | ApoH | 22,619.1 |
| APRIL | 334.6 | | | APRIL | 161.3 |
| | | Artemin | 2,703.0 | Artemin | 1,950.6 |
| Axl | 279.4 | Axl | 171.8 | Axl | 380.7 |
| B2M | 11,738.1 | B2M | 8,546.3 | B2M | 12,571.9 |
| BAFF | 1,283.4 | BAFF | 2,161.0 | BAFF | 110.0 |
| BCAM | 4,141.5 | BCAM | 1,113.1 | BCAM | 2,621.1 |
| BCMA | 243.9 | BCMA | 227.3 | BCMA | 282.4 |
| bFGF | 17.4 | bFGF | 59.8 | bFGF | 109.8 |
| bIG-H3 | 11,133.8 | bIG-H3 | 10,602.3 | bIG-H3 | 12,238.7 |
| BMP-2 | 71.1 | BMP-2 | 28.2 | BMP-2 | 54.3 |
| | | BMP-4 | 37.3 | | |
| BMP-5 | 163.0 | | | BMP-5 | 123.2 |
| | | BMP-6 | 15,624.1 | BMP-6 | 35,550.1 |
| BMP-7 | 1,874.8 | BMP-7 | 1,706.4 | BMP-7 | 1,670.0 |
| BTC | 157.6 | | | BTC | 72.4 |
| C5a | 495.7 | C5a | 248.1 | C5a | 838.0 |
| CA125 | 118,396.2 | CA125 | 81,267.7 | CA125 | 87,712.9 |
| CA15-3 | 524.9 | CA15-3 | 306.7 | CA15-3 | 473.7 |
| CA19-9 | 6,215.0 | CA19-9 | 36,363.9 | CA19-9 | 42,679.7 |

FIG. 3A

| | | | | | | | |
|---|---|---|---|---|---|---|---|
| CA9 | 164.6 | | CA9 | 258.5 | | CA9 | 211.9 |
| | | | Calbindin D | 866.1 | | Calbindin D | 695.8 |
| Cathepsin S | 1,785.6 | | Cathepsin S | 2,415.8 | | Cathepsin S | 1,970.6 |
| Cathepsin B | 6,177.0 | | Cathepsin B | 4,643.40 | | Cathepsin B | 2,273.10 |
| Cathepsin L | 315.3 | | Cathepsin L | 830.2 | | Cathepsin L | 489.3 |
| CCL28 | 417.8 | | CCL28 | 580.8 | | CCL28 | 789.3 |
| CD 40 | 190.1 | | CD 40 | 136.5 | | CD 40 | 163.7 |
| CD14 | 3,787.2 | | CD14 | 6,835.9 | | CD14 | 11,686.5 |
| CD163 | 9,213.8 | | CD163 | 8,742.1 | | CD163 | 5,132.7 |
| CD200 | 37.8 | | CD200 | 47.8 | | CD200 | 45.7 |
| CD23 | 49.6 | | CD23 | 379.1 | | CD23 | 277.7 |
| | | | | | | CD30 | 19.0 |
| CD40 L | 54.0 | | CD40 L | 73.7 | | CD40 L | 189.4 |
| CD97 | 226.9 | | CD97 | 1,036.9 | | CD97 | 1,553.2 |
| CEA | 1,286.4 | | CEA | 687.0 | | CEA | 871.1 |
| CEACAM-1 | 595.1 | | CEACAM-1 | 324.9 | | CEACAM-1 | 684.7 |
| Chemerin | 895.0 | | Chemerin | 1,141.2 | | Chemerin | 4,300.0 |
| CHI3L1 | 4,704.1 | | CHI3L1 | 4,135.3 | | CHI3L1 | 5,229.6 |
| | | | Ck beta 8-1 | 1,511.6 | | Ck beta 8-1 | 7,346.7 |
| Clusterin | 41,962.1 | | Clusterin | 32,987.0 | | Clusterin | 16,923.3 |
| | | | | | | CNTF | 181.7 |
| Cripto-1 | 29.9 | | Cripto-1 | 46.0 | | Cripto-1 | 340.1 |
| CRP | 5,867.6 | | CRP | 7,919.4 | | CRP | 700.5 |
| CRTAM | 56.1 | | CRTAM | 52.0 | | CRTAM | 31.8 |
| CTACK | 23.1 | | CTACK | 26.1 | | CTACK | 60.7 |
| | | | CTLA4 | 23.3 | | | |
| CXCL14 | 13,751.3 | | CXCL14 | 7,740.3 | | CXCL14 | 9,333.3 |
| CXCL16 | 3,988.4 | | CXCL16 | 5,351.5 | | CXCL16 | 4,797.1 |
| Cystatin C | 835,086.8 | | Cystatin C | 819,489.2 | | Cystatin C | 378,052.6 |
| DcR3 | 76.0 | | DcR3 | 641.3 | | DcR3 | 666.8 |
| Decorin | 250.7 | | Decorin | 3,842.8 | | Decorin | 3,887.9 |
| DKK-1 | 104,215.1 | | DKK-1 | 108,712.1 | | DKK-1 | 91,352.9 |
| Dkk-3 | 12,376.2 | | Dkk-3 | 17,006.2 | | Dkk-3 | 17,026.0 |
| | | | Dkk-4 | 50.1 | | Dkk-4 | 19.9 |
| DLL1 | 1,538.3 | | DLL1 | 3,559.6 | | DLL1 | 1,494.7 |
| DPPIV | 17,592.9 | | DPPIV | 16,680.9 | | DPPIV | 37,371.1 |
| DR6 | 9.9 | | DR6 | 9.0 | | DR6 | 12.4 |
| Dtk | 305.6 | | Dtk | 358.5 | | Dtk | 918.3 |
| E-Cadherin | 155.6 | | E-Cadherin | 144.1 | | E-Cadherin | 278.5 |
| EDA-A2 | 18.1 | | EDA-A2 | 24.9 | | EDA-A2 | 20.2 |
| EGF | 204.6 | | EGF | 93.2 | | EGF | 74.0 |
| EGF R | 2,493.3 | | EGF R | 1,486.0 | | EGF R | 2,868.6 |
| | | | EG-VEGF | 51.3 | | EG-VEGF | 174.2 |
| EMMPRIN | 350.7 | | EMMPRIN | 540.1 | | EMMPRIN | 472.8 |
| ENA-78 | 160.4 | | ENA-78 | 8,957.6 | | ENA-78 | 9,709.9 |
| Endoglin | 17.6 | | Endoglin | 11.6 | | Endoglin | 17.2 |
| Endostatin | 1,368.8 | | Endostatin | 1,441.2 | | Endostatin | 1,519.4 |
| | | | Eotaxin-2 | 9.0 | | | |
| Eotaxin-3 | 153.1 | | Eotaxin-3 | 165.1 | | Eotaxin-3 | 323.4 |
| | | | Epo R | 76.0 | | Epo R | 91.0 |

FIG. 3B

| | | | | | |
|---|---|---|---|---|---|
| ErbB2 | 45.2 | ErbB2 | 32.7 | ErbB2 | 48.1 |
| ErbB3 | 613.4 | ErbB3 | 602.4 | ErbB3 | 1,760.7 |
| E-Selectin | 319.3 | E-Selectin | 180.4 | E-Selectin | 137.0 |
| FABP2 | 148.1 | | | FABP2 | 73.4 |
| FAP | 10,787.1 | FAP | 12,080.1 | FAP | 12,845.0 |
| | | Fas | 23.6 | | |
| | | FAS L | 20.8 | FAS L | 9.1 |
| Fcr RIIBC | 466.5 | Fcr RIIBC | 897.9 | Fcr RIIBC | 569.4 |
| Ferritin | 29,170.8 | Ferritin | 20,108.3 | Ferritin | 17,620.3 |
| Fetuin A | 52,831.8 | Fetuin A | 22,865.3 | Fetuin A | 81,766.9 |
| FGF-19 | 26.7 | FGF-19 | 1.3 | FGF-19 | 31.9 |
| | | FGF-4 | 732.8 | FGF-4 | 1,158.3 |
| FGF-7 | 7,664.8 | FGF-7 | 2,950.1 | FGF-7 | 2,017.6 |
| | | FGF-9 | 17.3 | FGF-9 | 91.4 |
| Fibrinogen | 4,869.2 | Fibrinogen | 2,569.4 | Fibrinogen | 6,900.6 |
| FLRG | 6,832.9 | FLRG | 7,266.8 | FLRG | 10,755.3 |
| Flt-3L | 30.9 | Flt-3L | 64.4 | Flt-3L | 37.3 |
| Follistatin | 1,172.6 | Follistatin | 5,691.8 | Follistatin | 3,531.6 |
| FOLR1 | 24,218.1 | FOLR1 | 16,852.3 | FOLR1 | 41,664.7 |
| FSH | 481.0 | FSH | 40.3 | FSH | 77.3 |
| Furin | 5,253.2 | Furin | 9,961.9 | Furin | 8,636.2 |
| Galectin-3 | 3,503.1 | Galectin-3 | 2,604.6 | Galectin-3 | 2,031.3 |
| Galectin-7 | 36,814.6 | Galectin-7 | 34,917.9 | Galectin-7 | 47,133.6 |
| GASP-1 | 85.1 | GASP-1 | 380.6 | GASP-1 | 168.9 |
| GASP-2 | 1,208.4 | GASP-2 | 2,281.5 | GASP-2 | 480.5 |
| | | GCP-2 | 34.1 | GCP-2 | 64.6 |
| | | G-CSF | 1,018.6 | G-CSF | 430.5 |
| G-CSF R | 9.2 | G-CSF R | 22.8 | G-CSF R | 15.3 |
| GDF-15 | 1,449.8 | GDF-15 | 1,282.4 | GDF-15 | 1,138.6 |
| GH | 163.8 | GH | 138.5 | | |
| GITR | 76.5 | GITR | 111.5 | GITR | 124.0 |
| | | GITR Ligand | 2,938.6 | GITR Ligand | 2,073.3 |
| GRO | 5,249.7 | GRO | 6,191.7 | GRO | 6,516.5 |
| GROa | 7,058.2 | GROa | 4,261.1 | GROa | 8,436.0 |
| HAI-2 | 556.9 | HAI-2 | 978.6 | HAI-2 | 415.0 |
| HCC-1 | 752.4 | HCC-1 | 766.3 | HCC-1 | 697.4 |
| HCC-4 | 270.9 | HCC-4 | 241.4 | HCC-4 | 249.9 |
| hCGb | 24,149.6 | hCGb | 5,826.8 | hCGb | 28,868.3 |
| Hemoglobin | 1,719.1 | | | Hemoglobin | 4,926.8 |
| HGF | 1,719.3 | HGF | 1,712.10 | HGF | 2,696.5 |
| HGF R | 4,487.5 | HGF R | 4,436.8 | HGF R | 6,382.5 |
| | | HTRA2 | 3,263.9 | HTRA2 | 2,484.7 |
| HVEM | 358.5 | HVEM | 286.6 | HVEM | 429.6 |
| I-309 | 15.4 | I-309 | 25.9 | I-309 | 16.9 |
| ICAM-1 | 7,882.6 | ICAM-1 | 7,744.6 | ICAM-1 | 10,860.4 |
| ICAM-2 | 9,086.4 | ICAM-2 | 11,436.5 | ICAM-2 | 16,129.8 |
| IFNab R2 | 12.5 | IFNab R2 | 10.5 | IFNab R2 | 12.9 |
| IGFBP-1 | 7,743.1 | IGFBP-1 | 8,324.2 | IGFBP-1 | 7,382.5 |
| IGFBP-2 | 40,378.3 | IGFBP-2 | 43,118.4 | IGFBP-2 | 38,125.7 |
| IGFBP-3 | 121,736.1 | IGFBP-3 | 165,149.0 | IGFBP-3 | 156,044.6 |
| IGFBP-4 | 3,886.5 | IGFBP-4 | 17,936.5 | IGFBP-4 | 4,262.6 |

FIG. 3C

| | | | | | |
|---|---|---|---|---|---|
| IGFBP-5 | 288.5 | IGFBP-5 | 523.3 | IGFBP-5 | 57.8 |
| IGFBP-6 | 19,741.4 | IGFBP-6 | 23,931.0 | IGFBP-6 | 15,368.9 |
| IGF-I | 28.8 | IGF-I | 249.1 | IGF-I | 129.9 |
| IGF-I SR | 33.7 | IGF-I SR | 96.1 | IGF-I SR | 68.6 |
| | | | | IGF-II | 48.5 |
| IGF-II R | 524.3 | IGF-II R | 327.1 | IGF-II R | 1,123.9 |
| IL-1 R4 | 2,873.2 | IL-1 R4 | 1,956.0 | IL-1 R4 | 3,822.9 |
| | | IL-1 RI | 15.0 | | |
| | | | | IL-1 R6 | 8.2 |
| IL-1 sRII | 717.9 | IL-1 sRII | 721.9 | IL-1 sRII | 550.9 |
| IL-12p40 | 13.2 | IL-12p40 | 28.1 | | |
| IL-13 R1 | 203.7 | IL-13 R1 | 217.6 | IL-13 R1 | 111.4 |
| IL-13 R2 | 321.4 | IL-13 R2 | 413.9 | IL-13 R2 | 304.2 |
| | | IL-15 | 19.8 | | |
| IL-17B | 262.5 | IL-17B | 659.1 | IL-17B | 230.8 |
| IL-17B R | 2,169.0 | IL-17B R | 4,533.8 | IL-17B R | 1,011.3 |
| | | IL-17E | 5,166.9 | IL-17E | 6,174.3 |
| IL-17R | 24.4 | | | | |
| IL-18 Rb | 50.0 | IL-18 Rb | 28.8 | IL-18 Rb | 17.2 |
| IL-18 | 11.8 | IL-18 | 72.2 | | |
| IL-1F10 | 19.6 | IL-1F10 | 198.8 | IL-1F10 | 183.8 |
| IL-1F6 | 58.9 | IL-1F6 | 87.6 | IL-1F6 | 88.6 |
| | | IL-1F8 | 120.4 | IL-1F8 | 59.2 |
| IL-1F9 | 27.2 | | | IL-1F9 | 38.5 |
| IL-1R3 | 103.8 | IL-1R3 | 1,785.4 | IL-1R3 | 1,263.0 |
| | | IL-1R5 | 15.2 | IL-1R5 | 16.6 |
| IL-1ra | 1,743.5 | IL-1ra | 1,215.1 | IL-1ra | 1,129.7 |
| | | IL-2 | 11.6 | | |
| IL-2 Ra | 43.9 | IL-2 Ra | 61.1 | IL-2 Ra | 55.8 |
| IL-2 Rb | 517.9 | IL-2 Rb | 341.0 | IL-2 Rb | 315.5 |
| IL-2 Rg | 35.8 | IL-2 Rg | 17.7 | IL-2 Rg | 15.3 |
| | | IL-20 | 134.5 | | |
| IL-21 | 543.0 | IL-21 | 554.5 | IL-21 | 181.1 |
| IL-21R | 73.9 | IL-21R | 40.2 | IL-21R | 33.4 |
| IL-23 | 67.3 | IL-23 | 172.7 | IL-23 | 217.9 |
| IL-24 | 211.2 | IL-24 | 48.0 | IL-24 | 201.2 |
| IL-27 | 2,071.2 | IL-27 | 1,885.8 | IL-27 | 9,539.8 |
| IL-29 | 268.5 | | | IL-29 | 118.4 |
| | | IL-33 | 19.0 | IL-33 | 9.2 |
| | | IL-5 | 8.8 | | |
| | | IL-5 Ra | 76.0 | | |
| IL-6 | 561.3 | IL-6 | 362.8 | IL-6 | 308.9 |
| IL-6sR | 106.7 | IL-6sR | 223.8 | IL-6sR | 243.7 |
| IL-8 | 159.5 | IL-8 | 270 | IL-8 | 68.9 |
| Insulin | 13.3 | Insulin | 35.2 | Insulin | 12.4 |
| IP-10 | 1,092.6 | IP-10 | 1,514.9 | IP-10 | 1,003.9 |
| I-TAC | 39.9 | I-TAC | 56.0 | I-TAC | 55.0 |
| Kallikrein 14 | 23,888.8 | Kallikrein 14 | 29,158.9 | Kallikrein 14 | 86,782.8 |
| Lactoferrin | 54,384.5 | Lactoferrin | 53,191.2 | Lactoferrin | 50,637.7 |
| LAG-3 | 908.8 | LAG-3 | 952.5 | LAG-3 | 668.8 |
| LAP | 49.0 | LAP | 63.5 | LAP | 81.6 |

FIG. 3D

| | | | | | |
|---|---|---|---|---|---|
| Layilin | 482.2 | Layilin | 899.9 | Layilin | 1,215.3 |
| LDL R | 4,585.4 | LDL R | 5,446.7 | LDL R | 3,705.8 |
| Legumain | 24,834.7 | Legumain | 23,848.9 | Legumain | 39,624.5 |
| Leptin | 122.7 | Leptin | 1,869.0 | Leptin | 1,414.6 |
| | | Leptin R | 8.3 | Leptin R | 48.2 |
| LIF | 108.3 | LIF | 148.5 | LIF | 135.0 |
| LIMPII | 46.3 | LIMPII | 98.9 | LIMPII | 52.8 |
| Lipocalin-2 | 2,131.8 | Lipocalin-2 | 2,636.80 | Lipocalin-2 | 2,091.48 |
| LOX-1 | 3,581.8 | LOX-1 | 3,194.1 | LOX-1 | 3,333.5 |
| L-Selectin | 5,998.2 | L-Selectin | 6,540.3 | L-Selectin | 11,564.5 |
| | | Lymphotactin | 76.8 | | |
| LYVE-1 | 850.7 | LYVE-1 | 597.8 | LYVE-1 | 1,315.0 |
| Marapsin | 22,982.1 | Marapsin | 18,000.5 | Marapsin | 28,380.3 |
| MBL | 495.9 | MBL | 805.3 | MBL | 2,698.1 |
| MCP-1 | 768.7 | MCP-1 | 852.5 | MCP-1 | 935.2 |
| MCSF R | 20,550.8 | MCSF R | 21,588.0 | MCSF R | 14,561.0 |
| MDC | 13.8 | MDC | 56.4 | MDC | 83.8 |
| Mesothelin | 39,808.2 | Mesothelin | 164,754.4 | Mesothelin | 84,093.7 |
| MICB | 411.6 | MICB | 115.0 | MICB | 59.4 |
| MIF | 1,080.5 | MIF | 1,231.7 | MIF | 584.1 |
| MIG | 361.6 | MIG | 1,872.0 | MIG | 217.6 |
| MIP-1a | 9.2 | MIP-1a | 239.7 | | |
| MIP-1b | 11.9 | MIP-1b | 65.9 | MIP-1b | 17.3 |
| MIP-1d | 1,327.1 | MIP-1d | 2,801.8 | MIP-1d | 1,399.5 |
| MIP-3a | 13.6 | MIP-3a | 368.6 | MIP-3a | 303.9 |
| | | | | MIP-3b | 58.8 |
| MMP-1 | 87.5 | MMP-1 | 527.9 | MMP-1 | 901.5 |
| MMP-10 | 3,481.5 | MMP-10 | 4,172.6 | MMP-10 | 3,621.5 |
| MMP-2 | 1,855.1 | MMP-2 | 2,752.6 | MMP-2 | 2,410.7 |
| MMP-3 | 148.1 | MMP-3 | 402.2 | MMP-3 | 174.1 |
| MMP-7 | 3,954.8 | MMP-7 | 5,826.6 | MMP-7 | 5,082.7 |
| MMP-8 | 184.8 | MMP-8 | 2,242.0 | MMP-8 | 83.8 |
| | | MMP-9 | 51.3 | | |
| MPIF-1 | 180.8 | MPIF-1 | 984.7 | MPIF-1 | 121.9 |
| MSPa | 93.5 | MSPa | 21.1 | MSPa | 63.0 |
| NAP-2 | 501.1 | NAP-2 | 534.1 | NAP-2 | 626.3 |
| NCAM-1 | 1,890.9 | NCAM-1 | 1,704.4 | NCAM-1 | 2,914.9 |
| Neprilysin | 144.8 | Neprilysin | 68.4 | Neprilysin | 801.0 |
| NGF R | 18.8 | NGF R | 27.4 | | |
| Nidogen-1 | 1,934.3 | Nidogen-1 | 6,699.1 | Nidogen-1 | 498.3 |
| | | | | Notch-1 | 9.3 |
| NOV | 3,630.9 | NOV | 3,374.9 | NOV | 3,397.6 |
| NrCAM | 25.0 | NrCAM | 37.0 | NrCAM | 16.9 |
| NRG1-b1 | 41.7 | | | NRG1-b1 | 15.5 |
| NSE | 4,008.1 | NSE | 10,467.4 | NSE | 1,049.8 |
| | | NT-3 | 16.7 | | |
| OPG | 47.4 | OPG | 353.8 | OPG | 190.6 |
| OPN | 20,713.9 | OPN | 58,000.6 | OPN | 52,219.6 |
| OSM | 88.6 | | | OSM | 419.5 |

FIG. 3E

| | | | | | |
|---|---|---|---|---|---|
| Osteoactivin | 289.1 | Osteoactivin | 296.4 | Osteoactivin | 567.1 |
| PAI-I | 39,949.5 | PAI-I | 38,308.5 | PAI-I | 30,998.3 |
| PAPP-A | 10,303.9 | PAPP-A | 12,818.7 | PAPP-A | 57,461.4 |
| PARC | 13,978.2 | PARC | 15,832.6 | PARC | 16,339.5 |
| P-Cadherin | 30,524.7 | P-Cadherin | 30,712.0 | P-Cadherin | 50,053.3 |
| PD-1 | 55.5 | PD-1 | 33.1 | PD-1 | 70.5 |
| | | PD-ECGF | 29,811.2 | PD-ECGF | 16,035.9 |
| | | PDGF Ralpha | 5,748,070.1 | PDGF Ralpha | 2,533,983.7 |
| PDGF Rb | 469.1 | PDGF Rb | 478.3 | PDGF Rb | 96.9 |
| PDGF-AA | 60.1 | PDGF-AA | 61.4 | PDGF-AA | 46.2 |
| PDGF-AB | 70.4 | PDGF-AB | 100.6 | PDGF-AB | 155.2 |
| PECAM-1 | 46.8 | PECAM-1 | 142.8 | PECAM-1 | 24.6 |
| Pepsinogen I | 9,738.7 | Pepsinogen I | 9,123.8 | Pepsinogen I | 11,046.1 |
| Pepsinogen II | 5,374.0 | Pepsinogen II | 5,237.1 | Pepsinogen II | 4,356.0 |
| | | Periostin | 1,118,873.7 | Periostin | 6,383,891.6 |
| | | | | Persephin | 2,715.2 |
| | | PF4 | 9,733.9 | PF4 | 7,140.5 |
| PGRP-5 | 1,479.7 | PGRP-5 | 1,898.0 | PGRP-5 | 1,873.3 |
| Procalcitonin | 10.4 | Procalcitonin | 16.4 | Procalcitonin | 17.1 |
| Prolactin | 43,187.8 | Prolactin | 170,857.4 | Prolactin | 102,814.7 |
| Prostasin | 2,897.5 | Prostasin | 3,240.2 | Prostasin | 4,945.7 |
| PSA | 1,187.0 | PSA | 394.6 | PSA | 93.8 |
| PSMA | 326.7 | PSMA | 647.1 | PSMA | 406.4 |
| | | PTH | 2,322.5 | PTH | 1,673.0 |
| RAGE | 3,934.6 | RAGE | 4,641.2 | RAGE | 4,624.9 |
| RANK | 50.4 | RANK | 73.9 | RANK | 34.8 |
| | | RAP | 375.2 | RAP | 306.1 |
| RBP4 | 16,320.7 | RBP4 | 19,612.5 | RBP4 | 16,925.6 |
| Resistin | 2,688.6 | Resistin | 7,796.5 | Resistin | 9,279.8 |
| | | SAA | 79,326.4 | SAA | 94,411.3 |
| SCF | 13.4 | SCF | 67.0 | SCF | 34.2 |
| SCF R | 709.9 | SCF R | 497 | SCF R | 617.7 |
| | | SDF-1a | 25.6 | | |
| SDF-1b | 82.1 | SDF-1b | 118.4 | SDF-1b | 34.4 |
| Serpin A4 | 5,337.1 | Serpin A4 | 5,779.2 | Serpin A4 | 5,432.0 |
| | | Serpin F1 | 11,301.1 | Serpin F1 | 9,409.2 |
| sFRP-3 | 536.9 | sFRP-3 | 707.1 | sFRP-3 | 3,058.4 |
| sgp130 | 6,232.2 | sgp130 | 5,807.6 | sgp130 | 5,614.7 |
| | | Shh N | 62.1 | Shh N | 48.8 |
| | | SIGIRR | 330.7 | | |
| Siglec-5 | 643.2 | Siglec-5 | 1,320.0 | Siglec-5 | 1,973.4 |
| SOST | 744.4 | SOST | 764.9 | SOST | 605.2 |
| ST2 | 2,018.2 | ST2 | 2,281.7 | ST2 | 2,015.5 |
| Syndecan-1 | 567.5 | Syndecan-1 | 2,092.9 | Syndecan-1 | 1,533.7 |
| TACE | 407.1 | TACE | 27.3 | TACE | 615.6 |
| TACI | 227.5 | TACI | 233.4 | TACI | 70.9 |
| TF | 25.0 | TF | 34.5 | TF | 27.3 |
| TFPI | 1,807.6 | TFPI | 12,510.2 | TFPI | 11,412.5 |
| TGFb RIII | 777.3 | TGFb RIII | 770.2 | TGFb RIII | 1,548.0 |
| | | TGF-b2 | 8.3 | | |
| Thrombomodulin | 906.7 | Thrombomodulin | 1,157.3 | Thrombomodulin | 4,765.8 |

FIG. 3F

| | | | | | |
|---|---|---|---|---|---|
| Thyroglobulin | 473.1 | Thyroglobulin | 43.6 | Thyroglobulin | 91.7 |
| | | Tie-1 | 167.6 | Tie-1 | 339.7 |
| Tie-2 | 15.5 | | | Tie-2 | 24.2 |
| TIM-1 | 14.4 | TIM-1 | 18.2 | TIM-1 | 80.3 |
| TIMP-1 | 30,202.5 | TIMP-1 | 28,467.2 | TIMP-1 | 28,700.5 |
| TIMP-2 | 99,402.5 | TIMP-2 | 126,601.0 | TIMP-2 | 101,350.2 |
| TIMP-4 | 292.7 | TIMP-4 | 411.5 | TIMP-4 | 688.9 |
| TLR2 | 603.2 | TLR2 | 1,402.7 | TLR2 | 4,008.7 |
| TNF RI | 333.5 | TNF RI | 592.2 | TNF RI | 683.3 |
| TNF RII | 1,604.6 | TNF RII | 2,364.1 | TNF RII | 2,492.5 |
| tPA | 9.1 | tPA | 129.5 | tPA | 123.8 |
| TPO | 342.1 | TPO | 1,014.8 | TPO | 617.8 |
| | | TRAIL R2 | 32.3 | | |
| TRAIL R3 | 165.7 | TRAIL R3 | 219.8 | TRAIL R3 | 309.2 |
| TRAIL-R4 | 14.8 | TRAIL-R4 | 29.1 | TRAIL-R4 | 13.5 |
| TRANCE | 554.7 | TRANCE | 591.7 | TRANCE | 228.3 |
| Transferrin | 62,763.7 | Transferrin | 70,346.1 | Transferrin | 74,687.7 |
| Trappin-2 | 2,857.3 | Trappin-2 | 3,553.8 | Trappin-2 | 3,159.8 |
| TREM-1 | 68.6 | TREM-1 | 62.0 | TREM-1 | 53.8 |
| Troponin I | 962.1 | Troponin I | 4,463.1 | Troponin I | 485.1 |
| TSH | 25.4 | TSH | 11.2 | TSH | 19.7 |
| TSLP | 46.1 | TSLP | 8.0 | TSLP | 157.9 |
| TSP-1 | 50,496.6 | TSP-1 | 153,365.6 | TSP-1 | 99,608.5 |
| TSP-2 | 4,030.1 | TSP-2 | 4,173.9 | TSP-2 | 5,249.8 |
| TWEAK | 584.9 | TWEAK | 551.2 | TWEAK | 521.6 |
| uPA | 32.0 | uPA | 29.8 | uPA | 55.2 |
| uPAR | 9,959.0 | uPAR | 12,711.0 | uPAR | 16,939.5 |
| VCAM-1 | 6,282.9 | VCAM-1 | 2,945.5 | VCAM-1 | 13,039.5 |
| VE-Cadherin | 733.2 | VE-Cadherin | 2,225.0 | VE-Cadherin | 2,485.7 |
| VEGF | 25.6 | VEGF | 20.0 | VEGF | 21.9 |
| VEGF R1 | 68,624.2 | VEGF R1 | 91,111.7 | VEGF R1 | 62,766.1 |
| VEGF R2 | 627.7 | VEGF R2 | 370.6 | VEGF R2 | 393.4 |
| VEGF-C | 22.5 | VEGF-C | 23.8 | VEGF-C | 20.0 |
| | | VEGF-D | 41.8 | | |
| Vitronectin | 89,517.5 | Vitronectin | 466,728.2 | Vitronectin | 368,167.5 |
| vWF | 5,073.8 | vWF | 8,038.5 | vWF | 7,525.8 |
| WIF-1 | 290.0 | WIF-1 | 4,131.3 | WIF-1 | 3,089.2 |
| WISP-1 | 2,680.9 | WISP-1 | 11,313.4 | WISP-1 | 3,382.0 |

FIG. 3G

US 10,555,973 B2

THERAPEUTIC COMPOSITIONS

BACKGROUND

Amniotic fluid is a protective fluid contained within the amniotic sac that surrounds a fetus during pregnancy. The amniotic fluid can provide a number of developmental benefits to the fetus. For example, amniotic fluid allows the fetus to move in the womb, which can facilitate proper bone growth and development. Further, the amniotic fluid helps provide a constant temperature about the fetus and helps provide protection against impact or sudden movements.

The amniotic fluid can also facilitate the exchange of proper nutritional and developmental components between the mother and the fetus to support proper organ development. However, the composition of amniotic fluid typically changes over time. For example, during early stages of pregnancy the amniotic fluid is often primarily an aqueous electrolyte solution. By about week 12 to week 14, amniotic fluid begins to contain a variety of proteins, carbohydrates, lipids, urea, and the like.

The volume of amniotic fluid also changes over the duration of the pregnancy. For example, the amount of amniotic fluid typically increases in volume up until about week 28 to week 34 of the pregnancy. At this point in the pregnancy, there is typically about 800 milliliters of amniotic fluid present in the amniotic sac. However, in some cases, the volume of amniotic fluid can decrease to an amount from about 400 milliliters to about 600 milliliters by about week 42.

BRIEF DESCRIPTION OF THE DRAWINGS

For a fuller understanding of the nature and advantage of the present invention, reference is being made to the following detailed description of preferred embodiments and in connection with the accompanying drawings, in which:

FIGS. 3A-3G depict tables identifying various proteins present in three comparative samples of processed AF.

DESCRIPTION OF EMBODIMENTS

Figure 1:
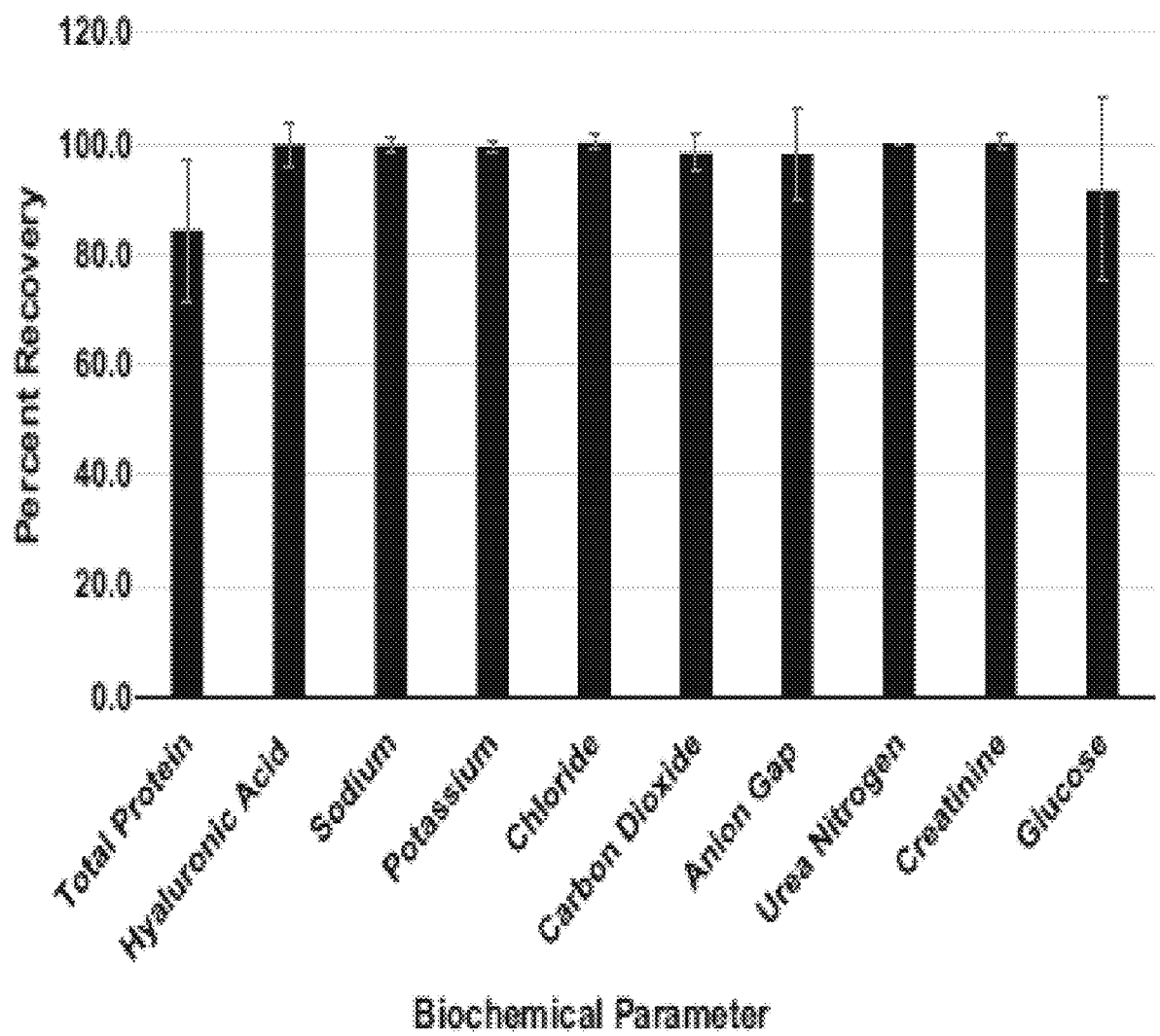
FIG. 1 depicts a chart of post-processing recoveries for various biochemical constituents. Percent recoveries for each parameter were determined by dividing post-processed amniotic fluid (AF) mean values by pre-processed AF mean values and multiplying by 100. Error bars represent standard deviation.
Figure 2A:
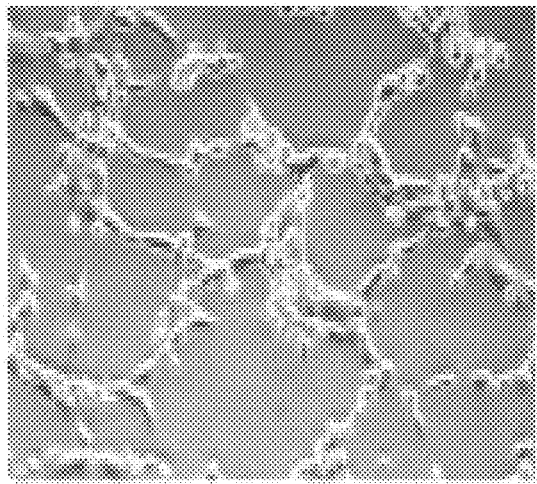
FIG. 2A depicts a representative image of a positive control HUVEC sample including endothelial tube formation (magnification 20x).
Figure 2B:
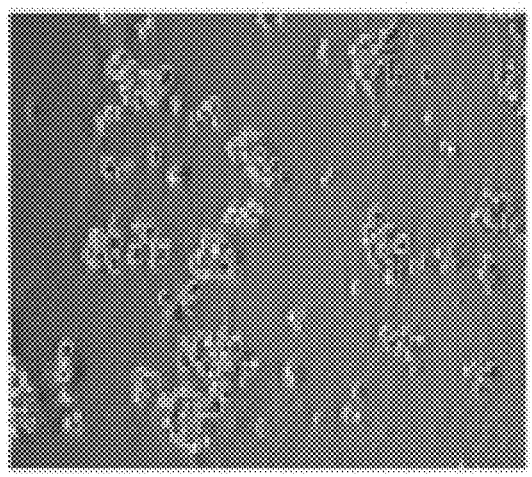
FIG. 2B depicts a representative image of a negative control HUVEC sample without endothelial tube formation (magnification 20x).
Figure 2C:
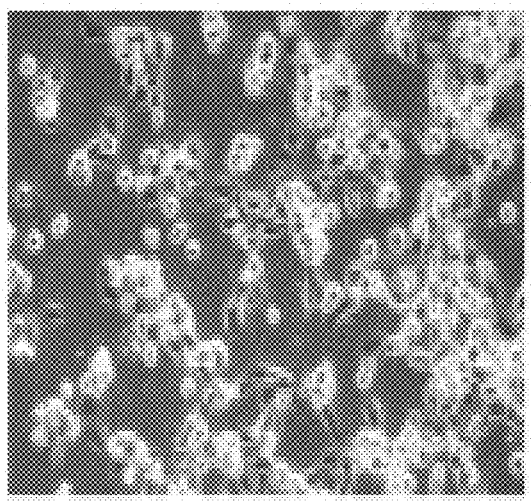
FIG. 2C depicts a representative image of HUVECs suspended with a portion of a first amniotic fluid that has not been processed (magnification 20x).
Figure 2D:
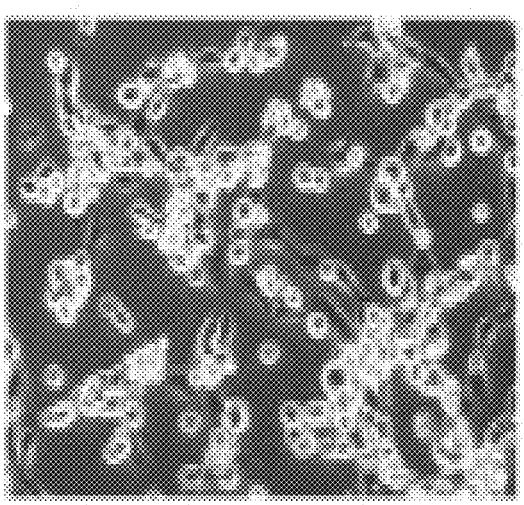
FIG. 2D depicts a representative image of HUVECs suspended with a portion of the first amniotic fluid that has been processed (magnification 20x).
Figure 2E:
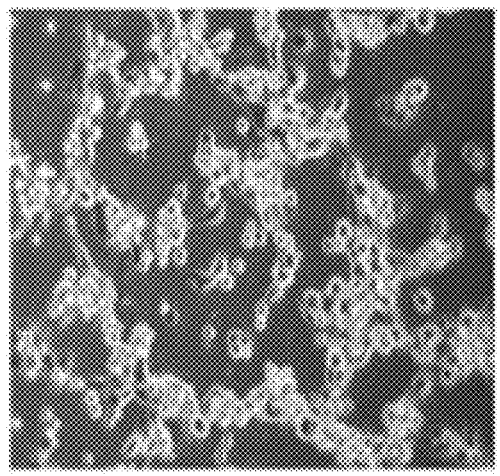
FIG. 2E depicts a representative image of HUVECs suspended with a portion of a second amniotic fluid that has not been processed (magnification 20x).
Figure 2F:
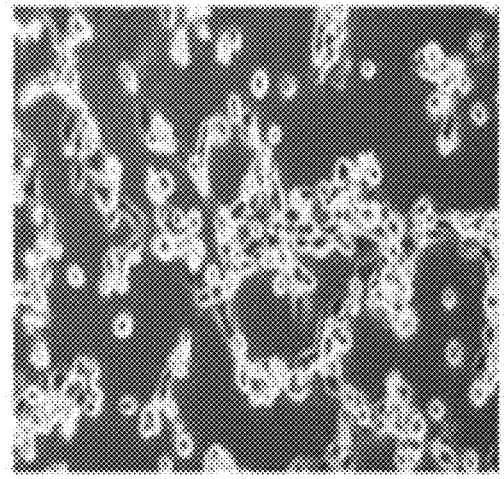
FIG. 2F depicts a representative image of HUVECs suspended with a portion of the second amniotic fluid that has been processed (magnification 20x).
Figure 2G:
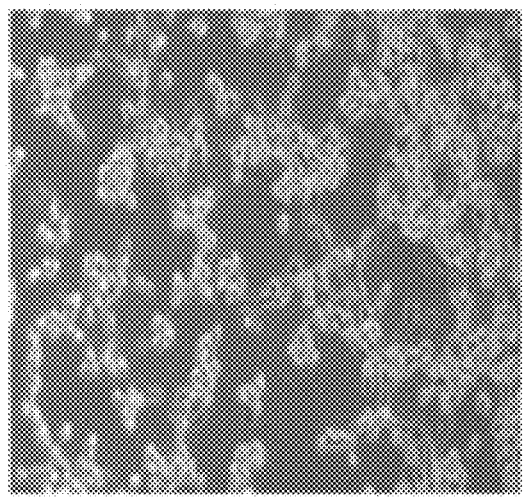
FIG. 2G depicts a representative image of HUVECs suspended with a portion of a third amniotic fluid that has not been processed (magnification 20x).
Figure 2H:
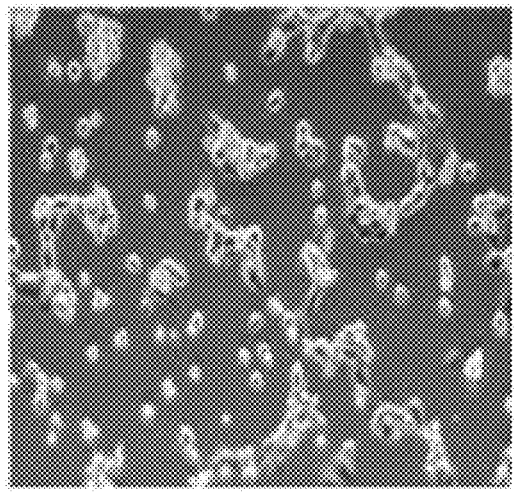
FIG. 2H depicts a representative image of HUVECs suspended with a portion of the third amniotic fluid that has been processed (magnification 20x).

Although the following detailed description contains many specifics for the purpose of illustration, a person of ordinary skill in the art will appreciate that many variations and alterations to the following details can be made and are considered to be included herein. Accordingly, the following embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

As used in this specification and the appended claims, the singular forms "a," "an" and "the" include plural referents unless the context clearly dictates otherwise. Thus, for example, reference to "polymer" can include a plurality of such polymers.

In this application, "comprises," "comprising," "containing" and "having" and the like can have the meaning ascribed to them in U.S. patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. patent law. "Consisting essentially of" or "consists essentially of" have the meaning generally ascribed to them by U.S. patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," in this written description it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 angstroms to about 80 angstroms" should also be understood to provide support for the range of "50 angstroms to 80 angstroms." Furthermore, it is to be understood that in this specification support for actual numerical values is provided even when the term "about" is used therewith. For example, the recitation of "about" 30 should be construed as not only providing support for values a little above and a little below 30, but also for the actual numerical value of 30 as well.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

The term "amniotic fluid agent" refers to any protein, hyaluronic acid (HA), or other component typically found in amniotic fluid to which an adverse health condition may be responsive and that is present in a therapeutic composition as described herein. In some examples, the "amniotic fluid agent" can be harvested with the amniotic fluid of the therapeutic composition, can be supplemented into the therapeutic composition, or a combination thereof.

The term "dosage unit" or "dose" are understood to mean an amount of an active agent that is suitable for administration to a subject in order achieve or otherwise contribute to a therapeutic effect. In some examples, a dosage unit can refer to a single dose that is capable of being administered to a subject or patient, and that may be readily handled and packed, remaining as a physically and chemically stable unit dose.

The phrase "effective amount," "therapeutically effective amount," or "therapeutically effective rate(s)" of an active ingredient refers to a substantially non-toxic, but sufficient amount or delivery rates of the active ingredient, to achieve therapeutic results in treating a disease or condition for which the drug is being delivered. It is understood that various biological factors may affect the ability of a substance to perform its intended task. Therefore, an "effective amount," "therapeutically effective amount," or "therapeutically effective rate(s)" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a subjective decision. The determination of a therapeutically effective amount or delivery rate is well within the ordinary skill in the art of pharmaceutical sciences and medicine.

As used herein, "formulation" and "composition" can be used interchangeably and refer to a combination of at least two ingredients. In some embodiments, at least one ingredient may be an active agent or otherwise have properties that exert physiologic activity when administered to a subject. For example, amniotic fluid includes at least two ingredients (e.g. water and electrolytes) and is itself a composition or formulation.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Reference in this application may be made to compositions, systems, or methods that provide "improved" or "enhanced" performance. It is to be understood that unless otherwise stated, such "improvement" or "enhancement" is a measure of a benefit obtained based on a comparison to compositions, systems or methods in the prior art. Furthermore, it is to be understood that the degree of improved or enhanced performance may vary between disclosed embodiments and that no equality or consistency in the amount, degree, or realization of improvement or enhancement is to be assumed as universally applicable.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

Example Embodiments

An initial overview of invention embodiments is provided below and specific embodiments are then described in further detail. This initial summary is intended to aid readers in understanding the technological concepts more quickly, but is not intended to identify key or essential features thereof, nor is it intended to limit the scope of the claimed subject matter.

The present disclosure is drawn to therapeutic compositions, methods of manufacturing therapeutic compositions, and methods of using therapeutic compositions to treat a subject having an adverse health condition that is responsive to treatment with the therapeutic compositions. In some examples, the therapeutic composition can include an amount of amniotic fluid having a therapeutically effective amount of at least one protein, hyaluronic acid (HA), or both. Further, the composition can be substantially free of lanugo, vernix, and cells harvested with or from the amniotic fluid.

In other examples, the therapeutic composition can include an amount of amniotic fluid and a therapeutically effective amount of at least one protein, HA, or both. In some examples, the therapeutically effective amount of at least one protein, HA, or both can already be present in the amount of amniotic fluid. In other examples, the therapeutically effective amount of at least one protein, HA, or both can be achieved through fortification or supplementation of the therapeutic composition with at least one protein, HA, or both. The composition can be substantially free of lanugo, vernix, and cells harvested with or from the amniotic fluid.

A method of manufacturing a therapeutic composition can include extracting or harvesting an amount of amniotic fluid from a pregnant female to provide an extracted or harvested amniotic fluid. The harvested amniotic fluid can include a therapeutically effective amount of at least one protein, hyaluronic acid, or both. The harvested amniotic fluid can be centrifuged to form a supernatant and a cell pellet. A portion of the supernatant can be filtered to prepare the therapeutic composition, which can be substantially free of lanugo, vernix, and cells harvested with or from the amniotic fluid.

A method of treating a subject with an adverse health condition responsive to treatment with an amniotic fluid agent can include administering a therapeutically effective amount of a therapeutic composition as recited herein.

With this overview in mind, the therapeutic compositions and associated methods will be described in further detail. Amniotic fluid (AF) can be a rich source of nutrients, cytokines, and growth factors that are valuable for fetal development and maturation. Additionally, AF can also contain stem cells with the potential to differentiate along multiple cell lineages. Further, AF can have a number of protective and regenerative properties, which can be provided via the exchange of water and solutes with surrounding tissues. This process can be accomplished via the utilization of different pathways during the course of a pregnancy that likely contribute to changes in the composition of the AF with gestational age.

Due to the beneficial combination of nutrients, cytokines, growth factors, and the like that are present in AF, a variety of adverse health conditions can be responsive to therapeutic treatment with AF. For example, in some cases, AF can inhibit the development of peritonitis. In other examples, AF can accelerate defense-repair mechanisms within damaged joints. In other examples, AF can have antimicrobial, immunomodulatory, and growth-promoting properties. Components with antimicrobial, antiviral, and anti-fungal activity that are present in AF can include lysozyme, peroxidase, transferrin, β-lysin, immunoglobulins, and zinc-peptide complexes, for example. Moreover, AF can provide a variety of immunomodulatory properties, such as suppression of pro-inflammatory responses resulting from various adverse health conditions, for example. Further, AF can provide a variety of growth promoting properties. As non-limiting examples, AF can enhance neochondrogenesis, regenerate peripheral nerves and bone, accelerate re-epithelialization in corneas, and promote healing of human skin wounds. Non-limiting examples of factors that are found in AF that can contribute to these activities can include inflammatory mediators that include TNF-α, IL-6, IL-1ra, IL-1 R4, Lactoferrin, IL8, and IL-10, trophic factors that include EGF, IGF-1, FGF, HGF, and TGF-α, and HA, which can be a valuable factor in promoting re-epithelialization in human skin wounds.

Thus, a therapeutic composition that includes an amount of amniotic fluid can be valuable in treating a variety of adverse health conditions. However, it can also be beneficial to remove a variety of components that are present in harvested amniotic fluid, such as lanugo, vernix, and cells present in the harvested amniotic fluid. Thus, the therapeutic composition can be processed to remove lanugo, vernix, and cells harvested with or from the amniotic fluid.

Processing of the amniotic fluid can also provide a variety of other properties that are not present in freshly harvested amniotic fluid. For example, the processed amniotic fluid can have a reduced amount of particulate matter as compared to unprocessed amniotic fluid. In some specific examples, the processed amniotic fluid can have less than 10,000 particles per ml of particles having a particle size of 10 microns or greater. In other examples, the processed amniotic fluid can have less than 5000 particles per ml of particles having a particle size of 10 microns or greater. In yet other examples, the processed amniotic fluid can have less than 1000, less than 500, or less than 300 particles per ml of particles having a particle size of 10 microns or greater.

In some additional examples, the processed amniotic fluid can have less than 300 particles per ml of particles having a particle size of 25 microns or greater. In other examples, the processed amniotic fluid can have less than 200 particles per ml of particles having a particle size of 25 microns or greater. In yet other examples, the processed amniotic fluid can have less than 100, less than 50, or less than 30 particles per ml of particles having a particle size of 25 microns or greater.

Processing of the amniotic fluid can also provide the amniotic fluid with a greater optical clarity (i.e. lower optical density) than freshly harvested amniotic fluid. For example, processed amniotic fluid can have an optical density of less than 0.20 when exposed to electromagnetic radiation at a wavelength of 590 nm, 570 nm, 550 nm, 540 nm, 500 nm, or 450 nm. In further examples, processed amniotic fluid can have an optical density of less than 0.15 when exposed to electromagnetic radiation at a wavelength of 590 nm, 570 nm, 550 nm, 540 nm, 500 nm, or 450 nm. In yet other examples, processed amniotic fluid can have an optical density of less than 0.10 when exposed to electromagnetic radiation at a wavelength of 590 nm, 570 nm, 550 nm, 540 nm, 500 nm, or 450 nm.

Processed amniotic fluid can also include a reduced amount of hemoglobin as compared to freshly harvested amniotic fluid. For example, processed amniotic fluid can include hemoglobin in an amount of from about 1 µg/ml to about 60 µg/ml. In other examples, processed amniotic fluid can include hemoglobin in an amount of from about 5 µg/ml to about 50 µg/ml. In yet other examples, processed amniotic fluid can include hemoglobin in an amount of from about 10 µg/ml to about 40 µg/ml.

While processing can remove some constituents from the amniotic fluid, a variety of beneficial constituents can also be largely preserved. For example, the processed amniotic fluid can retain a comparable amount of total protein as found in freshly harvested amniotic fluid. More specifically, total protein content for the amniotic fluid composition can typically be within the range of about 0.15 mg/ml to about 10 mg/ml. In some specific examples, the amniotic fluid can include from about 0.5 mg/ml to about 5 mg/ml of total protein. In yet other examples, the amniotic fluid can include from about 1 mg/ml to about 3.0 or 3.5 mg/ml of total protein.

Further, the processed amniotic fluid can still include effective amounts of HA. For example, HA can typically be present in the amniotic fluid in an amount greater than or equal to 150 ng/ml. In some specific examples, HA can be present in the amniotic fluid in an amount from about 150 ng/ml to about 500 ng/ml. In other examples, HA can be present in the amniotic fluid in an amount from about 350 ng/ml to about 450 ng/ml. In yet other examples, HA can be present in an amount from about 300 ng/ml to about 400 ng/ml, 410 ng/ml, or 420 ng/ml.

Further, the processed amniotic fluid can still include effective amounts of epidermal growth factor (EGF). For example, EGF can typically be present in the amniotic fluid in an amount greater than or equal to 100 ng/ml. In some specific examples, EGF can be present in the amniotic fluid in an amount from about 100 ng/ml to about 500 ng/ml. In other examples, EGF can be present in the amniotic fluid in an amount from about 100 ng/ml to about 400 ng/ml. In yet other examples, HA can be present in an amount from about 150 ng/ml to about 250 ng/ml.

It is noted that a variety of protein concentrations, HA concentrations, particles counts, optical densities, and the like are provided herein to help describe the processed amniotic fluid included in the therapeutic composition. Where such values are provided, these values generally refer to the processed amniotic fluid that is otherwise undiluted, unconcentrated, or a combination thereof, unless otherwise specified. However, this is not intended to exclude the use of diluted and/or concentrated amniotic fluid compositions. Thus, where the amount of amniotic fluid has been diluted, concentrated, or a combination thereof, the various values recited herein describing the amniotic fluid still apply to a corresponding amniotic fluid composition that is in an undiluted and/or unconcentrated state, unless otherwise specified.

As described above, a therapeutically effective amount of at least one protein, HA, or both can depend on a variety of factors. In many cases, a therapeutically effective amount can include the amounts recited above. However, in some cases, it can be desirable to either concentrate or dilute the amniotic fluid. In some examples, concentration of the amniotic fluid can be performed via evaporation, lyophilization, or other equivalent or similar process. In some specific examples, the amount of amniotic fluid can be or can include an amount of lyophilized amniotic fluid. Where this is the case, the lyophilized amniotic fluid can typically have a water content of from about 0.1 wt % to about 10 wt % prior to any desired subsequent dilution. The amniotic fluid can also be concentrated by fortifying or supplementing the amniotic fluid with at least one protein, HA, or both, as desired for a particular application of the therapeutic composition.

Thus, in some examples, the therapeutic composition can include only processed amniotic fluid, which can be diluted and/or concentrated as desired. In other examples, the therapeutic composition can be fortified or supplemented with at least one protein that can typically be naturally found in amniotic fluid. In yet other examples, the therapeutic composition can be fortified with HA. In some specific examples, the therapeutic composition can be fortified with a cytokine. In other specific examples, the therapeutic composition can be fortified with a growth factor, such as epidermal growth factor, for example. In additional examples, the therapeutic composition can be fortified with other constituents that can typically be naturally found in amniotic fluid, such as stem cells, nutrients, electrolytes, etc. In yet additional examples, the therapeutic composition can include an active agent that is not typically found in amniotic fluid.

Thus, the therapeutic composition can include a variety of additives and active agents. Non-limiting examples can include an anti-infective agent, an anti-tumor agent, an anti-inflammatory agent, a pain-controlling agent, an anti-rheumatic agent, a bisphosphonate, a supplementary growth factor, a supplementary cytokine, an amino acid, a protein, a vaccine, a hormone, a vitamin, a phytoestrogen, fluoride, the like, or combinations thereof.

Anti-infective agents can typically include a variety of active agents that can kill or prevent an infectious organism from spreading. Thus, anti-infective agents can include antibacterial agents, antifungal agents, antiviral agents, antiprotozoan agents, the like, or combinations thereof. Non-limiting examples can include amebicides such as chloroquine, nitazoxanide, paromomycin, tinidazole, metronidazole, iodoquinole, or the like; aminoglycosides such as tobramycin, gentamicin, amikacin, kanamycin, neomycin, streptomycin, or the like; anthelmintics such as albendazole, ivermectin, praziquantel, pyrantel, mebendazole, miltefosine, niclosamide, piperazine, thiabendazole, or the like; antifungals such as itraconazole, posaconazole, ketoconazole, fluconazole, clotrimazole, isavuconazole, miconazole, voriconazole, echinocandins, terbinafine, griseofulvin, flucytosine, nystatin, amphotericin b, or the like; antimalarials such as chloroquine, quinine, hydroxychloroquine, mefloquine, primaquine, pyrimethamine, halofantrine, doxycycline, or the like; antituberculosis agents such as aminosalicylic acid, bedaquiline, isoniazid, ethambutol, pyrazinamide, ethionamide, rifampin, rifabutin, rifapentine, capreomycin, cycloserine, streptomycin, or the like; antivirals such as amantadine, rimantadine, ritonavir, cobicistat, peginterferon alfa-2a, peginterferon alfa 2b, maraviroc, raltegravir, dolutegravir, elvitegravir, sofosbuvir, enfuvirtide, fomivirsen, foscarnet, oseltamivir, zanamivir, peramivir, etravirine, efavirenz, nevirapine, delavirdine, rilpivirine, daclatasvir, adefovir, entecavir, telbivudine, didanosine, tenofovir, abacavir, lamivudine, zidovudine, stavudine, emtricitabine, zalcitabine, boceprevir, simeprevir, fosamprenavir, lopinavir, darunavir, telaprevir, ritonavir, tipranavir, atazanavir, nelfinavir, amprenavir, indinavir, saquinavir, ganciclovir, valacyclovir, famciclovir, acyclovir, valganciclovir, ribavirin, cidofovir, or the like; carbapenems such as doripenem, meropenem, cilastatin, ertapenem, or the like; cephalosporins such as avibactam, ceftolozane, ceftazidime, tazobactam, cefadroxil, cephalexin, cefazolin, ceftaroline, loracarbef, cefotetan, cefuroxime, cefprozil, cefaclor, cefoxitin, ceftibuten, cefotaxime, ceftriaxone, cefpodoxime, cefixime, cefdinir, defditoren, ceftazidime, ceftizoxime, cefepime, or the like; glycopeptide antibiotics such as vancomycin, dalbavancin, oritavancin, telavancin, or the like; glycocyclines such as tigecycline, or the like; leprostatics such as thalidomide, dapsone, clofazimine, or the like; lincomycin, or the like; clindamycin, or the like; ketolides such as telithromycin, or the like; macrolides such as azithromycin, fidaxomicin, erythromycin, clarithromycin, or the like; antibiotics such as aztreonam, daptomycin, chloramphenicol, colistimethate, fosfomycin, rifaximin, metronidazole, sulfamethoxazole, atovaquone, bacitracin, dalfopristin, erythromycin, furazolidone, pentamidine, polymyxin b, spectinomycin, trimetrexate, linezolid, tedizolid, penicillins (e.g. ampicillin, amoxicillin, carbenicillin, piperacillin, ticarcillin, nafcillin, dicloxacillin, cloxacillin, oxacillin, or the like), quinolones (e.g. lomefloxacin, norfloxacin, ofloxacin, gatifloxacin, moxifloxacin, ciprofloxacin, levofloxacin, gemifloxacin, cinoxacin, nalidixic acid, sparfloxacin, or the like), sulfonamides (e.g. sulfamethoxazole, sulfadiazine, sulfisoxazole, or the like), tetracyclines (e.g. tetracycline, demeclocycline, doxycycline, minocycline, or the like), or the like; urinary anti-infectives such as methenamine, methylene blue, fosfomycin, nitrofurantoin, trimethoprim, cinoxacin, nalidixic acid, oxytetracycline, or the like; hydrates thereof, acids thereof, bases thereof, salts thereof, or combinations of any of such anti-infective agents.

In some examples, the therapeutic agent can also include any suitable antitumor agent. Non-limiting examples of antitumor agents can include angiogenesis inhibitors such as angiostatin k1-3, angiostatin k1-5, DL-α-difluoromethylornithine, endostatin, fumagillin, genistein, minocycline, staurosporine, (+/−)-thalidomide, or the like; DNA intercalators such as bleomycin, carboplatin, carmustine, chlorambucil, cisplatin, cyclophosphamide, cis-diammineplatinum(II) dichloride, melphalan, mitoxantrone, oxaliplatin, or the like; DNA synthesis inhibitors such as (+/−)-amethopterin, 3-amino-1,2,4-benzotraizine-1,4-dioxide, aminopterin, cytosine β-D-arabinofuranoside, 5-fluoro-5'-deoxyuridine, 5-fluorouracil, ganciclovir, hydroxyurea, mitomycin C, or the like; transcriptioin regulators such as actinomycin D, daunorubicin, doxorubicin, homoharringtonine, idarubicin, or the like; enzyme inhibitors such as S(+)-camptothecin, curcumin, (−)-deguelin, 5,6-dichlorobenzimidazole 1-β-D-ribofuranoside, etoposide, formestane, fostriecin, hispidin, 2-imino-1-imidazolidineacetic acid, mevinolin, trichostatin A, tyrphostin AG 34, tyrphostin AG 879, or the like; gene regulation agents such as 5-aza-2'-deoxycytidine, 5-azacytidine, cholecalciferol, 4-hydroxytamoxifen, melatonin, mifepristone, raloxifene, vitamin A aldehyde, vitamin A acid, vitamin A, 9-cis-retinoic acid, 13-cis-retinoic acid, tamoxifen, troglitazone, or the like; microtubule inhibitors such as colchicine, docetaxel, dolastatin 15, etoposide, irinotecan, nocodazole, paclitaxel, podophyllotoxin, rhizoxin, vinblastine, vincristine, vindesine, vinorelbine, or the like; other antitumor agents such as 17-(allylamino)-17-demethoxygeldanamycin, 4-amino-1,8-naphthalimide, apigenin, brefeldin A, cimetidine, dichloromethylene-diphosphonic acid, leuprolide, luteinizing hormone-releasing hormone, pifithrin-α, rapamycin, sex hormone-binding globulin, thapsigargin, bikunin, ifosfamide, temozolomide, capecitabine, methotrexate, gemcitabine, pemetrexed, mitomycin, epirubicin, bevacizumab, cetuximab, gefitinib, imatinib, trastuzamab, denosumab, rituximab, sunitinib, zoledronate, abiraterone, anastrozole, bicalutamide, exemestane, goserelin, medroxyprogesterone, octreotide, tamoxifen, bendamustine, lomustine, procarbazine, streptozocin, fludarabine, raltitrexed, mitoxantrone, eribulin, topotecan, afatinib, aflibercept, BCG, crizotinib, dabrafenib, interferon, ipilimumab, lapatinib, nivolumab, panitumumab, pembrolizumab, pertuzumab, sorafenib, trastuzumab emtansine, temsirolimus, vemurafenib, ibandronic acid, pamidronate, bexarotene, buserelin, cyproterone, degarelix, folinic acid, fulvestrant, lanreotide, lenalidomide, letrozole, leuprorelin, megestrol, mesna, thalidomide, or the like; hydrates thereof, acids thereof, bases thereof, salts thereof, or combinations of any of such antitumor agents.

In some examples, the therapeutic composition can also include any suitable anti-inflammatory agent. Non-limiting examples of anti-inflammatory agents can include ibuprofen, naproxen, aspirin, diclofenac, celecoxib, sulindac, oxaprozin, piroxicam, indomethacin, meloxicam, fenoprofen, difunisal, etodolac, ketorolac, meclofenamate, nabumetone, salsalate, ketoprofen, tolmetin, flurbiprofen, mefenamic acid, famotidine, bromfenac, nepafenac, prednisone, cortisone, hydrocortisone, methylprednisolone, deflazacort, prednisolone, fludrocortisone, amcinonide, betamethasone diproprionate, clobetasol, clocortolone, dexamethasone, diflorasone, durasteride, flumethasone pivalate, flunisolide, fluocinolone acetonide, fluocinonide, fluorometholone, fluticasone propionate, flurandrenolide, hydroflumethiazide, the like, hydrates thereof, acids thereof, bases thereof, or salts thereof, or combinations thereof.

In some examples, the therapeutic composition can also include any suitable pain-controlling agent. Non-limiting examples of pain controlling agents can include anti-inflammatory agents, such as those listed above, acetaminophen, codeine, dihydrocodeine, tramadol, meperidine, hydrocodone, oxycodone, morphine, fentanyl, hydromorphone, buprenorphine, methadone, diamorphine, pethidine, the like, hydrates thereof, acids thereof, bases thereof, or salts thereof, or combinations thereof.

In some examples, the therapeutic composition can also include any suitable anti-rheumatic agent. Non-limiting examples of anti-rheumatic agents can include methotrexate, sulfasalazine, chloroquine, hydroxychloroquine, leflunomide, azathioprine, cyclosporine, minocycline, abatacept, rituximab, tocilizumab, anakinra, adalimumab, etanercept, infliximab, cetolizumab, golimumab, D-penicillamine, auranofin, the like, hydrates thereof, acids thereof, bases thereof, or salts thereof, or combinations thereof.

In some examples, the therapeutic composition can also include any suitable bisphosphonate. Non-limiting examples of bisphosphonates can include alendronate, etidronate, zoledronate, ibandronate, alendronate, risedronate, pamidronate, tiludronate, clodronate, neridronate, olpadronate, the like, hydrates thereof, acids thereof, bases thereof, or salts thereof, or combinations thereof.

In some examples, the therapeutic composition can also include any suitable growth factor. Non-limiting examples of supplementary growth factors can include platelet-derived growth factor (PDGF), epidermal growth factor (EGF), transforming growth factor-alpha (TGF-α), fibroblast growth factor (FGF), nerve growth factor (NGF), erythropoietin, transforming growth factor-beta (TGF-β), insulin-like growth factor-1 (IGF-1), insulin-like growth factor-2 (IGF-2), the like, or combinations thereof.

In some examples, the therapeutic composition can also include any suitable supplementary cytokine. Non-limiting examples of supplementary cytokines can include interleukins, lymphokines, monokines, interferons, colony stimulating factors, chemokines, the like, or combinations thereof.

In some examples, the therapeutic composition can also include any suitable amino acid. Non-limiting examples can include arginine, histidine, isoleucine, leucine, lysine, methionine, phenylalanine, tryptophan, valine, acetyl-L-carinitine arginate, alpha-aminoadipic acid, alpha-amino-N-butyric acid, beta-alanine, beta-amino-isobutyric acid, carnosine, citruline, gamma-amino butyric acid, hydroxyproline, 1-methylhistidine, 3-methylhistidine, N-acytyl-L-cysteine, ornithine, para-aminobenzoic acid, phosphoserine, phosphoethanolamine, taurine, the like, isomers thereof, hydrates thereof, salts thereof, acids thereof, bases thereof, or any combinations thereof.

In some examples, the therapeutic composition can also include any suitable protein. Non-limiting examples can include cytokines and/or growth factors, such as those listed above, as well as antibodies, Fc-fusion proteins, anticoagulants, blood factors, bone morphogenetic proteins, engineered protein scaffolds, enzymes, hormones, thrombolytics, the like, or combinations thereof.

In some examples, the therapeutic composition can also include a vaccine. Non-limiting examples of vaccines can include adenovirus vaccine, coxsackie B vaccine, cytomegalovirus vaccine, dengue vaccine, Eastern equine encephalitis vaccine, ebola vaccine, enterovirus vaccine, Epstein-barr vaccine, hepatitis A vaccine, hepatitis B vaccine, hepatitis C vaccine, hepatitis E vaccine, HIV vaccine, human papillomavirus vaccine, HTLV-1 T-lymphotrophic vaccine, influenza vaccine, Japanese encephalitis vaccine, Marburg vaccine, measles vaccine, mumps vaccine, norovirus vaccine, polio vaccine, rabies vaccine, respiratory syncytial virus (RSV) vaccine, rotavirus vaccine, rubella vaccine, severe acute respiratory syndrome (SARS) vaccine, varicella vaccine, smallpox vaccine, West Nile virus vaccine, yellow fever vaccine, anthrax vaccine, DPT vaccine, Q fever vaccine, Hib vaccine, tuberculosis vaccine, meningococcal vaccine, typhoid vaccine, pneumococcal vaccine, cholera vaccine, caries vaccine, ehrlichiosis vaccine, leprosy vaccine, lyme disease vaccine, *Staphylococcus aureus* vaccine, *Streptococcus pyogenes* vaccine, syphilis vaccine, tularemia vaccine, *Yersinia pestis* vaccine, the like, or combinations thereof.

In some examples, the therapeutic composition can also include a hormone. Non-limiting examples of hormones can include progestogens, androgens, estrogens, somatostatins, growth hormones, thyroid hormones, glucocorticoids, the like, or combinations thereof.

In some examples, the therapeutic composition can also include a vitamin. Non-limiting vitamins can include vitamin A, vitamin B1, vitamin B2, vitamin B6, vitamin B12, vitamin C, vitamin D, vitamin E, vitamin H, vitamin K, folic acid, the like, or combinations thereof.

In some examples, the therapeutic composition can also include a variety of additional supplementary agents, such as phytoestrogens, fluoride, calcium, iron, magnesium, zinc, any other suitable active agent, or combinations thereof. In some additional examples, the therapeutic composition can include tissue or other cells obtained or derived from the placenta, bone marrow, the umbilical cord, amniotic membrane, amniotic-chorionic membrane, adipose tissue, peripheral blood, or the skin, for example. In some specific examples, the cells can be stem cells. In some examples, the stem cells can be cells that are reprogrammed to function as stem cells. In some examples, the cells can be osteogenic cells.

In some examples, various active and/or supplementary agents can be added directly to the amniotic fluid without addition of other constituents. However, in other examples, the therapeutic composition can further comprise a pharmaceutically acceptable carrier to facilitate delivery of the amniotic fluid, the active and/or supplementary agent, or both. Where a pharmaceutically acceptable carrier is employed, the amniotic fluid combined with the pharmaceutically acceptable carrier can be in either liquid or solid form (e.g. lyophilized amniotic fluid). Further, the pharmaceutically acceptable carrier can be formulated to provide a therapeutic composition that can be administered via various modes of administration. For example, the pharmaceutically acceptable carrier can be formulated to administer the therapeutic composition via injection, enteral administration, topical administration, transdermal administration, transmucosal administration, inhalation, implantation, or the like.

In some examples, the pharmaceutically acceptable carrier can be formulated to provide a therapeutic composition for administration via injection, such as intramuscular injection, intravenous injection, subcutaneous injection, intradermal injection, intrathecal injection, intraocular injection, or the like. In such examples, the pharmaceutically acceptable carrier can include a variety of components, such as water, a solubilizing or dispersing agent, a tonicity agent, a pH adjuster or buffering agent, a preservative, a chelating agent, a bulking agent, the like, or a combination thereof.

In some examples, an injectable therapeutic composition can include a solubilizing or dispersing agent. Non-limiting examples of solubilizing or dispersing agents can include polyoxyethylene sorbitan monooleates, lecithin, polyoxyethylene polyoxypropylene co-polymers, propylene glycol, glycerin, ethanol, polyethylene glycols, sorbitol, dimethylacetamide, polyethoxylated castor oils, n-lactamide, cyclodextrins, carboxymethyl cellulose, acacia, gelatin, methyl cellulose, polyvinyl pyrrolidone, the like, or combinations thereof.

In some examples, an injectable therapeutic composition can include a tonicity agent. Non-limiting examples of tonicity agents can include sodium chloride, potassium chloride, calcium chloride, magnesium chloride, mannitol, sorbitol, dextrose, glycerin, propylene glycol, ethanol, trehalose, phosphate-buffered saline (PBS), Dulbecco's PBS, Alsever's solution, Tris-buffered saline (TBS), water, balanced salt solutions (BSS), such as Hank's BSS, Earle's BSS, Grey's BSS, Puck's BSS, Simm's BSS, Tyrode's BSS, and BSS Plus, the like, or combinations thereof. The tonicity agent can be used to provide an appropriate tonicity of the therapeutic composition. In one aspect, the tonicity of the therapeutic composition can be from about 250 to about 350 milliosmoles/liter (mOsm/L). In another aspect, the tonicity of the therapeutic composition can be from about 277 to about 310 mOsm/L.

In some examples, an injectable therapeutic composition can include a pH adjuster or buffering agent. Non-limiting examples of pH adjusters or buffering agents can include a number of acids, bases, and combinations thereof, such as hydrochloric acid, phosphoric acid, citric acid, sodium hydroxide, potassium hydroxide, calcium hydroxide, acetate buffers, citrate buffers, tartrate buffers, phosphate buffers, triethanolamine (TRIS) buffers, the like, or combinations thereof. Typically, the pH of the therapeutic composition can be from about 5 to about 9, or from about 6 to about 8.

In some examples, an injectable therapeutic composition can include a preservative. Non-limiting examples of preservatives can include ascorbic acid, acetylcysteine, bisulfate, metabisulfite, monothioglycerol, phenol, meta-cresol, benzyl alcohol, methyl paraben, propyl paraben, butyl paraben, benzalkonium chloride, benzethonium chloride, butylated hydroxyl toluene, myristyl gamma-picolinium chloride, 2-phenoxyethanol, phenyl mercuric nitrate, chlorobutanol, thimerosal, tocopherols, the like, or combinations thereof.

In some examples, an injectable therapeutic composition can include a chelating agent. Non-limiting examples of chelating agents can include ethylenediaminetetra acetic acid, calcium, calcium disodium, versetamide, calteridol, diethylenetriaminepenta acetic acid, the like, or combinations thereof.

In some examples, an injectable therapeutic composition can include a bulking agent. Non-limiting examples of bulking agents can include sucrose, lactose, trehalose, mannitol, sorbitol, glucose, rafinose, glycine, histidine, polyvinyl pyrrolidone, the like, or combinations thereof.

In yet other examples, the pharmaceutically acceptable carrier can be formulated to provide a therapeutic composition for enteral administration, such as via solid oral dosage forms or liquid oral dosage forms. In the case of solid oral dosage forms, the pharmaceutically acceptable carrier can include a variety of components suitable for forming a capsule, tablet, or the like. In the case of a liquid dosage form, the pharmaceutically acceptable carrier can include a variety of components suitable for forming a dispersion, a suspension, a syrup, an elixir, or the like.

In some specific examples, the therapeutic composition can be formulated as a tablet. In such examples, the therapeutic composition can typically include a binder. Non-limiting examples of binders can include lactose, calcium phosphate, sucrose, corn starch, microcrystalline cellulose, gelatin, polyethylene glycol (PEG), polyvinyl pyrrolidone (PVP), hydroxypropyl cellulose, hydroxyethylcellulose, carboxymethyl cellulose (CMC), the like, or combinations thereof.

Where the therapeutic composition is formulated as a tablet, in some examples the therapeutic composition can also include a disintegrant. Non-limiting examples of disintegrants can include crosslinked PVP, crosslinked CMC, modified starch, sodium starch glycolate, the like, or combinations thereof.

In some examples the tablet can also include a filler. Non-limiting examples of fillers can include lactose, dicalcium phosphate, sucrose, microcrystalline cellulose, the like, or combinations thereof.

In some further examples, the tablet can include a coating. Such coatings can be formed with a variety of materials, such as hydroxypropyl methylcellulose (HPMC), shellac, zein, various polysaccharides, various enterics, the like, or combinations thereof.

In some examples, the tablet can include a variety of other ingredients, such as anti-adherents (e.g. magnesium stearate, for example), colorants, glidants (e.g. fumed silica, talc, magnesium carbonate, for example), lubricants (e.g. talc, silica, magnesium stearate, stearic acid, for example) preservatives, desiccants, and/or other suitable tablet excipients, as desired.

In some other examples, the therapeutic composition can be formulated as a capsule. In such examples, the capsule itself can typically include gelatin, hypromellose, HPMC, CMC, the like, or combinations thereof. A variety of excipients can also be included within the capsule, such as binders, disintegrants, fillers, glidants, preservatives, coatings, the like, or combinations thereof, such as those listed above with respect to tablets, for example, or other suitable variations.

In some examples, the therapeutic composition can be formulated as a liquid oral dosage form. A liquid oral dosage form can include a variety of excipients, such as a liquid vehicle, a solubilizing agent, a thickener or dispersant, a preservative, a tonicity agent, a pH adjuster or buffering agent, a sweetener, the like, or a combination thereof. Non-limiting examples of liquid vehicles can include water, ethanol, glycerol, propylene glycol, the like, or combinations thereof. Non-limiting examples of solubilizing agents can include banzalkonium chloride, benzethonium chloride, cetylpyridinium chloride, docusate sodium, nonoxynol-9, octoxynol, polyoxyethylene polyoxypropylene co-polymers, polyoxyl castor oils, polyoxyl hydrogenated castor oils, polyoxyl oleyl ethers, polyoxyl cetylstearyl ethers, polyoxyl stearates, polysorbates, sodium lauryl sulfate, sorbitan monolaurate, sorbitan monooleate, sorbitan monopalmitate, sorbitan monostearate, tyloxapol, the like, or combinations thereof. Non-limiting examples of thickeners or dispersants can include sodium alginate, methylcellulose, hydroxyethylcellulose, hydroxypropylcellulose, HPMC, CMC, microcrystalline cellulose, tragacanth, xanthangum, bentonite, carrageenan, guar gum, colloidal silicon dioxide, the like, or combinations thereof. The preservative, tonicity agent, pH adjuster or buffering agent can typically be any of those described above with respect to the injectable formulations or other suitable preservative, tonicity agent, pH adjuster or buffering agent. Sweeteners can include natural and/or artificial sweeteners, such as sucrose, glucose, fructose, stevia, erythritol, xylitol, aspartame, sucralose, neotame, acesulfame potassium, saccharin, advantame, sorbitol, the like, or combinations thereof, for example.

In yet other examples, the pharmaceutically acceptable carrier can be formulated to provide a therapeutic composition for topical, transdermal, or transmucosal administration, such as to the skin, to the eye, to the vaginal cavity, to the rectum, to the nasal cavity, the like, or a combination thereof. Further, the topical formulations can be formulated for local and/or systemic delivery of one or more components of the therapeutic composition.

Where the therapeutic composition is formulated for topical, transdermal, or transmucosal administration, the pharmaceutically acceptable carrier can include a variety of components suitable for forming a suspension, dispersion, lotion, cream, ointment, gel, foam, patch, powder, paste, sponge, the like, or a combination thereof. Non-limiting examples can include a solubilizer, an emulsifier, a dispersant, a thickener, an emollient, a pH adjuster, a tonicity agent, a preservative, an adhesive, a penetration enhancer, the like, or a combination thereof. Non-limiting examples of solubilizers and/or emulsifiers can include water, ethanol, propylene glycol, ethylene glycol, glycerin, polyethylene glycol, banzalkonium chloride, benzethonium chloride, cetylpyridinium chloride, docusate sodium, nonoxynol-9, octoxynol, polyoxyethylene polyoxypropylene co-polymers, polyoxyl castor oils, polyoxyl hydrogenated castor oils, polyoxyl oleyl ethers, polyoxyl cetylstearyl ethers, polyoxyl stearates, polysorbates, sodium lauryl sulfate, sorbitan monolaurate, sorbitan monooleate, sorbitan monopalmitate, sorbitan monostearate, tyloxapol, the like, or combinations thereof. In some examples, the solubilizer can also include a hydrocarbon or fatty substance, such as petrolatum, microcrystalline wax, paraffin wax, mineral oil, ceresi, coconut oil, bees wax, olive oil, lanolin, peanut oil, spermaceti wax, sesame oil, almond oil, hydrogenated castor oils, cotton seed oil, soybean oil, corn oil, hydrogenated sulfated castor oils, cetyl alcohol, stearyl alcohol, oleyl alcohol, lauryl alcohol, myristyl alcohol, stearic acid, oleic acid, palmitic acid, lauraic acid, ethyl oleate, isopropyl myristicate, the like, or combinations thereof. In some examples, the solubilizer can include a silicon, such as polydimethylsiloxanes, methicones, dimethylpropylsiloxanes, methyl phenyl polysiloxanes, steryl esters of dimethyl polysiloxanes, ethoxylated dimethicones, ethoxylated methicones, the like, or combinations thereof.

In some additional examples, the therapeutic composition can include a dispersant and/or thickening agent, such as polyacrylic acids (e.g. Carbopols, for example), gelatin, pectin, tragacanth, methyl cellulose, hydroxylethylcellulose, hydroxypropylcellulose, HPMC, CMC, alginate, starch, polyvinyl alcohol, polyvinyl pyrrolidone, co-polymers of polyoxyethylene and polyoxypropylene, polyethylene glycol, the like, or combinations thereof.

In some examples, the therapeutic composition can include an emollient, such as aloe vera, lanolin, urea, petrolatum, shea butter, cocoa butter, mineral oil, paraffin, beeswax, squalene, jojoba oil, coconut oil, sesame oil, almond oil, cetyl alcohol, stearyl alcohol, olive oil, oleic acid, triethylhexanoin, glycerol, sorbitol, propylene glycol, cyclomethicone, dimethicone, the like, or combinations thereof.

In some examples, the therapeutic composition can include an adhesive, such as acrylic adhesives, polyisobutylene adhesives, silicon adhesives, hydrogel adhesives, the like, or combinations thereof.

In some examples, the therapeutic composition can include a penetration enhancer, such as ethanol, propylene glycol, oleic acid and other fatty acids, azone, terpenes, terpenoids, bile acids, isopropyl myristate and other fatty esters, dimethyl sulphoxides, N-methyl-2-pyrrolidone and other pyrrolidones, the like, or combinations thereof.

The pH adjusters, tonicity agents, and preservatives in the topical, transdermal, or transmucosal therapeutic composition can generally include those pH adjusters and buffering agents, tonicity agents, and preservative agents listed above, or any other suitable pH adjusters, buffering agent, tonicity agent, or preservative for a particular formulation and/or use thereof. In some examples, the therapeutic composition can also include fumed silica, mica, talc, titanium dioxide, kaolin, aluminum glycinate, ethylenediaminetetraacetic acid, fragrances, colorants, other components as described above, the like, or combinations thereof.

In some additional examples, the pharmaceutically acceptable carrier can be formulated for administration via inhalation. In some examples, such formulations can include a propellant, such as hydrofluoralkanes, such as HFA134a, HFA227, or other suitable propellant. In yet other examples, the therapeutic composition can be formulated for administration via nebulization. In either case, the therapeutic composition can also include a variety of solubilizing agents, such as those described above. In other examples, the therapeutic composition can be formulated as a dry powder aerosol. In some examples, the therapeutic composition can include a particulate carrier and/or other particulate excipients, such as lactose, mannitol, other crystalline sugars, fumed silica, magnesium stearate, amino acids, the like, or combinations thereof.

In some specific examples, the pharmaceutically acceptable carrier can be formulated to provide a therapeutic composition for ocular administration. Non-limiting examples can include topical application to the eye in the form of a drop, a gel, a film, an insert, a sponge, an ointment, the like, or a combination thereof. In yet other examples, the therapeutic composition can be formulated for intraocular injection or implantation in the form of a solution, a depot, a scaffold, the like, or a combination thereof. Ocular compositions can include a variety of excipients, such as water, a tonicity agent, a thickening agent, a biodegradable polymer, a solubilizing agent, an emulsifier, a preservative, the like, or other suitable component, or a combination thereof. In some examples, the ocular composition can include a biodegradable polymeric matrix that can include a variety of biodegradable constituents, such as polylactic acid, poly (lactic-co-glycolic) acid, polyglycolic acid, poly(caprolactone), hyaluronic acid, polyhydroxybutyrate, polyvinyl alcohol, polyvinylpyrrolidone, carbomers, polyacrylic acid, polyoxyethylene/polyoxypropylene copolymers, other copolymers, albumins, casein, zein, collagen, other proteins, glucose, sucrose, maltose, trehalose, amylose, dextrose, fructose, mannose, galactose, other sugars, erythritol, threitol, arabitol, xylitol, ribitol, mannitol, sorbitol, galactitol, fucitol, iditol, inositol, volemitol, isomalt, maltitol, lactitol, maltotriitol, maltotetraitol, polyglycitol, other sugar alcohols, chondroitin and/or other glycosaminoglycans, inulin, starches, acacia gum, agar, carboxymethyl cellulose, methyl cellulose, ethyl cellulose, alginates, carrageenan, cassia gums, cellulose gums, chitin, chitosan, curdlan, gelatin, dextran, fibrin, fulcelleran, gellan gum, ghatti gum, guar gum, tragacanth, karaya gum, locust bean gum, pectin, starch, tara gum, xanthan gum, and other polysaccharides, and functionalized derivatives of any of the above, copolymers thereof, the like, or mixtures thereof. It is noted that these biodegradable polymers can also be used in a variety of formulations other than ocular formulations.

In some specific examples, the pharmaceutically acceptable carrier can be formulated to provide a therapeutic composition for use as a bone graft material, such as a demineralized bone graft matrix (DBM) putty, gel, or the like. In some examples, the pharmaceutically acceptable carrier can include a bone graft material, such as demineralized bone powder, hydroxyl apatite, calcium phosphate, various calcium salts, the like, or combinations thereof. In some examples, the pharmaceutically acceptable carrier can also include a tonicity agent, such as those described above. In some examples, the pharmaceutically acceptable carrier can also include a variety of other constituents. Non-limiting examples can include carboxymethyl cellulose, DL alpha-tocopherol and other mixed tocopherols, polyhydroxy compounds (e.g., ethylene glycol, diethylene glycol, triethylene glycol, 1,2-propanediol, glycerol, trimethylolethane, trimethylopropane, erythritol, pentaerythritol, polyalkylene glycols, polyethylene glycols, polyvinylalcohols, xylitol, sorbitol, mannitol, dulcitol, arabinose, xylose, ribose, adonitol, arabitol, rhamose, inositol, fructose, galactose, glucose, mannose, sorbose, sucrose, dextrose, maltose, lactose, maltitol, lactitol, stachyose, maltopentaose, cyclomaltohexaose, carrageenan, agar, dextran, alginic acid, guar gum, gum tragacanth, locust bean gum, gum arabic, xanthan gum, amylose and mixtures thereof), natural polymers (e.g., fibrin, collagen, and gelatin and mixtures thereof), natural and semi-synthetic polysaccharides (e.g., hyaluronic acid, dextran, dextran sulfate, chondroitin sulfate, dermatan sulfate, keratin sulfate, heparin, heparan sulfate, alginate, pectin, starch, hydroxalkylmethylcelluloses, hydroxyethylmethylcellulose, hydroxypropylmethylcellulose, methylcellulose, carboxymethylcellulose, mixtures thereof, and pharmaceutically acceptable salts and derivatives), synthetic polymers (e.g., polylactic acid, polyglycolic acid, copolymers of lactic and glycolic acid, polyvinyl alcohol, polycarylic acid, polypropylene glycol (PPG), polyethylene glycol (PEG), polyethylene oxide (PEO), polypropylene oxide (PPO), and copolymers of PPG/PPO and PEG/PEO forming Pluronics, water soluble polyacrylates, and water soluble polymethacrylates, polyvinyl alcohol, polyvinylprrolidone, hydrolyzed poly-acrylonitrile, hydrolyzed polyacrylamide, and polyacrylic acid), and/or any other suitable components as described herein.

In some other specific examples, the pharmaceutically acceptable carrier can be formulated to provide a therapeutic composition for use as a biocompatible injectable adhesive, such as to facilitate bone repair and growth. In some examples, the pharmaceutically acceptable carrier can include a bone graft material, such as demineralized bone powder, hydroxyl apatite, calcium phosphate, various calcium salts, the like, or combinations thereof. In some examples, the pharmaceutically acceptable carrier can also include fibrin, gelatin, cayanoacrylate, histoacryl, dermabond, methyl methacrylate, zinc phosphate, epoxy, resins, pieces of DBM, surface adhesives, demineralized bone powder, bone morphogenic proteins (i.e., BMP1, BMP2, OP1, or the like), and/or other suitable components.

It is noted that a number of compositional excipients are disclosed above with specific reference to particular types of formulations. However, it is noted that any excipients disclosed herein, or other suitable excipients, can be used with any type of therapeutic composition, where suitable, whether or not a particular excipient or type of excipient is specifically described in connection with that type of therapeutic composition. Therefore, the therapeutic compositions described herein can be formulated in a variety of ways for various modes of administration.

The present disclosure also provides methods of manufacturing a therapeutic composition. The methods can include harvesting or extracting amniotic fluid from a pregnant female to provide a harvested amniotic fluid. In some examples, the harvested amniotic fluid can include a therapeutically effective amount of at least one protein, HA, or both. The therapeutically effective amount can be determined by volume, concentration of at least one protein, concentration of HA, the like, or a combination thereof. For example, in some cases, the volume of the harvested amniotic fluid can be small, but the concentration of the at least one protein and/or HA can remain at a suitable concentration, or vice versa. In either case, the harvested amniotic fluid can still have a therapeutically effective amount of at least one protein, HA, or both.

The amniotic fluid can be harvested in a variety of ways. In some examples, harvesting can include performing an abdominal fenistil incision through the abdominal and uterine muscles without cutting into the amnion membrane. In further detail, in some cases, the amnion membrane can also be allowed to herniate out via the incision to allow facile access to the amnion membrane. In some examples, this method of harvesting (i.e. not cutting the amnion membrane and/or allowing the amnion membrane to herniate out via the incision) can substantially prevent or minimize the collection of blood. A suction catheter can then be inserted into the amnion membrane, such as by blunt end insertion of the catheter into the amnion membrane, for example. The suction catheter can be fluidly connected to a sterile suction container. The amniotic fluid can be suctioned or aspirated into the sterile suction container. In one specific example, an AF collection system can include a sterile suction container, sterile tubing, and a soft wall suction catheter that allows aspiration of the AF from the birth sac through the sterile tubing into the sterile suction container.

In some examples, the harvested amniotic fluid can be centrifuged to form a supernatant and a cell pellet. Centrifugation can typically be performed at a relative centrifugal force of from about 1000×g to about 1800×g. In some additional examples, centrifugation can be performed at a relative centrifugal force of from about 1200×g to about 1600×g. However, the particular relative centrifugal force employed can also affect the centrifugation time. Centrifugation can typically be performed for a period of from about 5 minutes to about 60 minutes. In yet other examples, centrifugation can be performed for a period of from about 10 minutes to about 30 minutes. Further, centrifugation can typically be performed at a temperature of from about 1° C. to about 10° C., or from about 2° C. to about 6° C.

A portion of the supernatant can be filtered to prepare a therapeutic composition that is substantially free of lanugo, vernix, and cells harvested with or from the amniotic fluid. Filtration can be performed in any suitable manner. In some specific examples, filtration can be performed by passing the supernatant through a first filter to prepare a filtered supernatant and subsequently passing the filtered supernatant through a second filter to prepare the therapeutic composition. Where this is the case, in some examples, the first and second filters can be loaded into a common housing. In yet other examples, the first filter and second filter can be loaded into independent housings that are fluidly connected.

In some examples, the harvested amniotic fluid can be filtered to produce a supernatant. Filtration can typically be performed by first using filters from about 40 to 70 μm and then a second filter from about 0.1 μm to 0.2 μm. Filtration can typically be performed at a temperature from about 1° C. to about 25° C. A variety of filter chemistries can be used and any suitable filter chemistry is considered within the scope of the present method. In some examples, the filter chemistry of the first filter, the second filter, or both can include polyethersulfone, cellulose acetate, cellulose nitrate, nylon, glass fiber, or the like.

In some examples, the therapeutic composition can include at least 60%, 70%, 80% or 90% of the total protein present in the harvested amniotic fluid. In some additional examples, the therapeutic composition can include from about 70% to about 90% of the total protein present in the harvested amniotic fluid. In yet further examples, the therapeutic composition can include from about 80% to about 95% of the total protein present in the harvested amniotic fluid.

In some additional examples, the therapeutic composition can include at least 80%, 90%, or 95% of the HA present in the harvested amniotic fluid. In some additional examples, the therapeutic composition can include from about 80% to about 95%, 98%, or 99% of the HA present in the harvested amniotic fluid. In yet further examples, the therapeutic composition can include from about 90% to about 100% of the HA present in the harvested amniotic fluid.

In some further examples, the method of manufacturing the therapeutic composition can also include lyophilizing the therapeutic composition. Any suitable lyophilization process can be used to lyophilize the therapeutic composition. In some examples, lyophilizing the AF or the therapeutic composition can be performed in multiple segments. For example, a first segment can be performed at a temperature ramp of from about 0.2° C./min to about 1° C./min (e.g. 0.5° C./min, for example) to a holding temperature of about −35° C. to about −45° C. (e.g. −40° C., for example) where the temperature can be maintained for a period of from about 2 hours to about 5 hours (e.g. a 3 hour period, for example). In additional examples, a second segment can be performed at a temperature ramp of from about 1° C./min to about 3° C./min (e.g. about 1.5° C./min) to a holding temperature of from about −10° C. to about −30° C. (e.g. about −20° C., for example) where the temperature can be maintained for a period of from about 5 hours to about 15 hours (e.g. about 10 hours, for example). In yet further examples, a third segment can be performed at a temperature ramp of from about 1° C./min to about 3° C./min (e.g. about 1.5° C./min, for example) to a holding temperature of from about 0° C. to about 10° C. (e.g. 5° C., for example) and maintained for a period of from about 5 hours to about 15 hours (e.g. about 8 hours, for example). In some examples, the dry weight can be from about 4 wt % to about 9 wt % of the original weight the AF or therapeutic composition.

The present disclosure also provides methods of treating a subject with an adverse health condition responsive to treatment with an amniotic fluid agent. The method can include administering a therapeutically effective amount of a therapeutic composition as described herein to a subject.

The therapeutic compositions described herein can be used to treat a variety of adverse health conditions. Non-limiting examples can include a wound, a respiratory condition, an inflammatory condition, chronic pain, a urological condition, a skeletal condition, an ophthalmic condition, a cardiovascular condition, a neurological condition, a digestive condition, a reproductive condition, a cosmetic condition, the like, or combinations thereof.

In some examples, the therapeutic composition can be used to treat a wound, or a symptom thereof. Non-limiting types of wounds that can be treated include abrasions, lacerations, contusions, penetrating wounds (e.g. cuts, surgical wounds, puncture wounds, etc.), thermal wounds, chemical wounds, electrical wounds, bite wounds, sting wounds, the like, or combinations thereof. Further, the method can be used to treat external wounds, internal wounds, or both.

In some examples, the therapeutic composition can be used to treat a respiratory condition, or a symptom thereof. Non-limiting examples of respiratory conditions can include asthma, emphysema, chronic obstructive pulmonary disease, acute respiratory virus, sinusitis, bronchitis, cystic fibrosis, tuberculosis, tonsillitis, otitis media, pharyngitis, laryngitis, pneumonia, lymphoma, pleural mesothelioma, lung cancers, pulmonary edema, acute respiratory disease syndrome, pneumoconiosis, the like, or combinations thereof.

In some examples, the therapeutic composition can be used to treat an inflammatory condition, or a symptom thereof. Non-limiting examples of inflammatory conditions can include ankylosing spondylitis, antiphospholipid antibody syndrome, gout, rheumatoid arthritis, myositis, scleroderma, Sjogren's syndrome, lupus, vasculitis, the like, or a combination thereof.

In some examples, the therapeutic composition can be used to treat chronic pain or the symptom of pain. Non-limiting sources of chronic pain can include chronic inflammation, post-surgical pain, post-trauma pain, lower back pain, cancer, arthritis, neurogenic pain, migraines and other headaches, the like, or combinations thereof.

In some examples, the therapeutic composition can be used to treat a urological condition, or a symptom thereof. Non-limiting examples of urological conditions can include urinary incontinence, scrotum inflammation, erectile dysfunction, Peyronie's disease, benign prostatic hyperplasia, urinary tract infections, prostate cancer, bladder cancer, bladder prolapse, interstitial cystitis, prostatitis, the like, or combinations thereof.

In some examples, the therapeutic composition can be used to treat a skeletal condition, or a symptom thereof. Non-limiting examples of a skeletal condition can include a fracture, kyphosis, lordosis, scoliosis, arthritis, rheumatoid arthritis, bone cancer, gout, osteoporosis, rickets, the like, or combinations thereof. The method can also be used to facilitate new bone growth and/or in connection with implantation of bone grafts. In some specific examples, a therapeutic composition can be injected or implanted into fractured vertebrae to provide re-expansion of the vertebra, support of the vertebra, and/or facilitate new bone growth to help restore structure and function to the vertebra, and/or other affected bones.

In some examples, the therapeutic composition can be used to treat an ophthalmic condition, or a symptom thereof. Non-limiting examples of ophthalmic conditions can include basal cell carcinoma, central retinal artery occlusion, central retinal vein occlusion, vitreous detachment, retinal break, retinal detachment, age-related macular degeneration, swollen optic disc, glaucoma, choroidal melanoma, iris melanoma, ischemic optic neuropathy, retinoblastoma, retinopathy of prematurity, strabismus, amblyopia, optic neuritis, refractive disorders, cataracts, the like, or combinations thereof.

In some examples, the therapeutic composition can be used to treat a cardiovascular condition, or a symptom thereof. Non-limiting examples can include aneurysm, atherosclerosis, high blood pressure, peripheral arterial disease, angina, coronary artery disease, coronary heart disease, heart attack, heart failure, stroke, transient ischemic attacks, pericardial disease, heart valve disease, congenital heart disease, cardiomyopathy, pericardial disease, aorta disease, Marfan syndrome, vascular disease, rheumatic heart disease, the like, or combinations thereof.

In some examples, the therapeutic composition can be used to treat a neurological condition, or a symptom thereof. Non-limiting examples of neurological conditions can include Parkinson's disease, Alzheimer's disease, spina bifida, stroke, injuries to the spinal cord, injuries to the brain, brain tumors, meningitis, the like, or combinations.

In some examples, the therapeutic composition can be used to treat a digestive condition, or a symptom thereof. Non-limiting examples of a digestive condition can include acid reflux, abdominal adhesions, appendicitis, Barrett's esophagus, celiac disease, colon polyps, Crohn's disease, diverticulosis, diverticulitis, diabetes, gall stones, gastritis, gastroparesis, gastrointestinal bleeding, hemorrhoids, inguinal hernia, irritable bowel syndrome, lactose intolerance, liver disease, Menetrier's disease, microscopic colitis, pancreatitis, ulcers, proctitis, ulcerative colitis, viral gastroenteritis, whipple disease, the like, or combinations thereof.

In some examples, the therapeutic composition can be used to treat a reproductive disorder, or a symptom thereof. Non-limiting examples of reproductive disorders can include cervical cancer, prostate cancer, breast cancer, ovarian cancer, penile cancer, vaginal cancer, uterine cancer, testicular cancer, impotence, sexual arousal disorder, hypogonadism, dysmenorrhea, chlamydia, gonorrhea, endometriosis, syphilis, the like, or combinations thereof.

In some examples, the therapeutic composition can be used to treat a cosmetic condition. Non-limiting examples of cosmetic conditions can include skin wrinkles, skin laxity, crows feet, scarring (including surgical and non-surgical scarring), hair loss (including eyelashes and eyebrows), hyperpigmentation, acne, rosacea, dark circles or darkened skin beneath the eye, sun spots, birth marks, varicose veins, spider veins, stretch marks, ingrown hairs, moles, cleft palate and other birth defects, the like, or combinations thereof.

Further, the therapeutic composition can be administered in any suitable way. Non-limiting examples can include administration via injection, enteral administration, topical administration, transdermal administration, transmucosal administration, inhalation, implantation, or a combination thereof.

The therapeutically effective amount can depend on a variety of factors, such as the condition to be treated, the subject to be treated, dosage regimens, or the like. For example, in some cases, the therapeutically effective amount can be administered via a single dose and/or a dosage regimen. In some examples, the dosage regimen can include administering the therapeutic composition at a suitable frequency. In some examples, the dosage regimen can include administering the therapeutic composition from 1 time per day to 12 times per day or more in individual doses. In some further examples, the dosage regimen can include administering the therapeutic composition from 1 time per day to 2, 3, 4, or 6 times per day in individual doses. In yet other examples, the therapeutic composition can be administered via infusion, or other equivalent process. Where this is the case, in some examples, the composition can be administered over a period of from about 30 minutes or 1 hour to about 6 hours or 12 hours or more. Further, depending on the adverse health condition, administration of the therapeutic composition can be performed over a period of from 1 day to 365 days or more, over a period from 1 day to 30 days, over a period of 7 days to 90 days, over a period of 1 month to 6 months, 12 months, 18 months, or 24 months, or other suitable treatment period at any suitable frequency, such as those described above, or other suitable frequency, such as once per week, twice per week, three times per week, once every two weeks, once per month, once every six weeks, once every two months, etc.

In some specific examples, a therapeutically effective amount can include an amount of total protein from about 0.1 mg to about 2500 mg per dose. In other examples, a therapeutically effective amount can include an amount of total protein from about 0.5 mg to about 10 mg, from about 5 mg to about 50 mg, or from about 10 mg to about 100 mg per dose. In yet other examples, the therapeutically effective amount can include an amount of total protein from about 50 mg to about 500 mg, from about 100 mg to about 1000 mg, or from about 750 mg to about 2500 mg per dose.

In some additional examples, a therapeutically effective amount can include an amount of HA from about 0.01 µg to about 350 µg per dose. In other examples, a therapeutically effective amount can include an amount of total protein from about 0.05 µg to about 1 µg, from about 0.5 µg to about 5 µg, or from about 1 µg to about 10 µg per dose. In yet other examples, the therapeutically effective amount can include an amount of total protein from about 5 µg to about 50 µg, from about 10 µg to about 100 µg, or from about 75 µg to about 350 µg per dose.

In some additional examples, a therapeutically effective amount can include an amount of epidermal growth factor (EGF) from about 0.01 µg to about 200 µg per dose. In other examples, a therapeutically effective amount can include an amount of total protein from about 0.01 µg to about 0.5 µg, from about 0.1 µg to about 2 µg, or from about 0.5 µg to about 5 µg per dose. In yet other examples, the therapeutically effective amount can include an amount of total protein from about 1 µg to about 20 µg, from about 10 µg to about 100 µg, or from about 50 µg to about 200 µg per dose.

In some examples, the therapeutically effective amount can include a volume therapeutic composition of from about 0.1 ml to about 1000 ml dose. In yet other examples, the therapeutically effective amount can include a volume from about 0.25 ml to about 5 ml, from about 0.5 ml to about 10 ml, or from about 1 ml to about 50 ml dose. In yet other examples, the therapeutically effective amount can include a volume from about 20 ml to about 500 ml, from about 250 ml to about 750 ml, or from about 500 ml to about 1000 ml per dose.

EXAMPLES

Example 1—Collection and Evaluation of Amniotic Fluid

Materials and Methods

Donor Consent, Screening and Infectious Disease Testing

To participate in the study, women were required to be 18 years or older with an uncomplicated singleton pregnancy. Informed consent was obtained from women who were scheduled to undergo a C-section. As part of the donor selection process, medical and social history screening was performed using a self-administered questionnaire designed to ask broad leading questions to determine the health of the potential donor and to minimize any communicable risks to the recipient. Donors were selected based on medical and social history responses that met the Standards of the American Association of Tissue Banks. Maternal blood samples were collected prior to delivery and infectious disease testing was performed for HBsAg (Hepatitis B surface antigen), HBcAb (Hepatitis B core antibody), HCV (Hepatitis C antibody screen and HCV nucleic acid test), HIV I/II-Ab (Human Immunodeficiency Virus Types 1 and 2 antibody and HIV nucleic acid test), Syphilis (RPR test), and CMV (antibody screen).

Amniotic Fluid Collection

A physician executed abdominal fenistil incision was performed through the abdominal and uterine muscles without cutting into the amnion membrane. Using a sterile soft suction catheter connected to a sterile MediVac Suction Container (Cardinal Health, Waukegan, Ill.), a blunt end insertion with a catheter was made into the amnion membrane and the amniotic fluid (AF) was aseptically suctioned into a MediVac Container. The container was labelled, wrapped in frozen Insul-ice mats (Fisher Scientific, Hanover Park, Ill.) and placed in a temperature monitored shipper that is validated for transport between 2° C. and 8° C. to the test facility. Upon arrival at the facility, the product was immediately placed in a refrigerator at 2-8° C. until processing occurred.

Processing

The MediVac container with AF was aseptically placed in a biological safety cabinet and the AF was transferred via aseptic techniques into sterile centrifuge tubes. The total volume and gross appearance of the AF were recorded and samples were removed for sterility testing, cell counts, and other relevant testing. The AF was centrifuged at 1400×g for 20 min at 4° C. Once centrifugation was complete, the supernatant was expressed into a new transfer pack and the remaining cell pellet was characterized and cultured as described below. The supernatant from the AF was filtered to sterilize and eliminate cellular debris from the final product.

Cell Counts, Cell Cultures, and Flow Cytometry

Cell pellets were re-suspended in Dulbecco's phosphate-buffered saline (Life Technologies Corporation, Grand Island, N.Y.) and passed through a 40 µM sterile cell strainer (BD Biosciences, Durham, N.C.) to remove non-cellular material/aggregates. The filtered material was centrifuged at 400×g for 10 min and the resulting isolate was assessed by microscopic evaluation. Manual cell counts and viabilities were performed using trypan blue (Sigma-Adrich, St. Louis, Mo.).

Cell pellets were isolated from freshly collected AF and were plated on tissue culture-treated plastic at 500 cells/cm$^2$ in Prime XV AFSC® (Amniotic Fluid Stem Cell) expansion medium (Irvine Scientific, Santa Ana, Calif.). This typically generated focal adherent populations of cells. The focal outgrowths were trypsinized, re-established as a monolayer, and passaged multiple times.

After the final passage, the harvested cells were immunophenotyped using fluorescence-conjugated mouse anti-human monoclonal antibodies: CD90-fluorescein isothiocyanate (CD90-FITC), CD73-allophycocyanin (APC), CD166-phycoerythrin (PE), CD14-PE, CD34-APC, CD45-peridinin-chlorophyll protein, HLA-DR-FITC, and HLA-ABC-FITC. Appropriate isotype controls were set up in parallel (antibodies were obtained from BD Biosciences, San Jose, Calif.). The cells were incubated for 30-60 min at 4° C. in the dark and were washed in phosphate-buffered saline containing 0.5% bovine serum albumin. A minimum of 10,000 events were collected using a Cyflow Space, Sysmex-Partec flow cytometer (Sysmex; Lincolnshire, Ill.). Data acquisition and analysis was performed using Flow-Max software.

Tri-Lineage Differentiation

Adipogenic and osteogenic induction was performed using a modification of the manufacturer's instructions (STEMPRO® Adipogenesis and Osteogenesis Differentiation Kits; Gibco Life Technologies). Briefly, adherent cells were removed from culture by adding 0.05 mL/cm$^2$ of 0.05% trypsin-ethylenediamine tetraacetic acid. The cells were centrifuged and resuspended in Prime XV AFSC and the cells were seeded at 10,500 cells/cm$^2$ for adipogenic and osteogenic differentiation in six well plates. Cells were maintained at 37° C. in a humidified atmosphere of 5% $CO_2$. After a couple of days in culture, the medium was replaced with either adipocyte differentiation medium or osteocyte differentiation medium and the cells were cultured for an additional 14-15 days. Differentiation medium was changed every 2-3 days. Staining was initiated by fixing cells with 10% formalin and the cells were made permeable with isopropanol. Adipocytes were stained by applying oil red 0 for 5 min and osteocytes by adding 2% alizarin red S for 20 min and counterstaining with hematoxylin for 1 min. Before visualization on an inverted light microscope, the wells were washed with deionized water.

Chondrocyte differentiation was also performed using the manufacturer's instructions (STEMPRO® Chondrogenesis Differentiation Kit). Mesenchymal stem cells (MSCs) were harvested and cells were resuspended with an appropriate volume of pre-warmed MesenPRO RS medium at a concentration of $1.6 \times 10^7$ viable cell/mL. Micromass cultures were generated by seeding 5 µL of the cell solution into each well of a 6-well plate, incubating the cells for 2 h and then adding chondrogenesis differentiation medium to the culture vessels. Differentiation medium was changed every 2-3 days and after 21 days of culture, cells were fixed with 10% formalin and stained with 1% Alcian Blue.

Chemistry and Sterility Testing

Chemistry assessments for sodium, potassium, chloride, urea nitrogen, creatinine, and hyaluronic acid (HA) were performed by a contract testing facility. Total protein levels were determined using a BioRad Bradford Protein Assay Kit (Life Technologies, Grand Island, N.Y.). Pre-processing microbiologic testing was performed for aerobic, anaerobic and fungal microorganisms using the BACTEC system (Becton-Dickinson, Sparks, Md.). BACTEC Plus Aerobic/F, Plus Anaerobic/F, and a Myco F/Lytic culture bottles were each inoculated with 1 mL of AF. The bottles were sent to the testing facility for a 5 day culture and microorganism detection. Post-processing or final product 14-day sterility testing was performed using United States Pharmacopeia guidelines. This was accomplished by sending aliquots of AF to a separate testing facility for further testing.

Endothelial Tube Formation

Endothelial tube formation assays were performed using an in vitro angiogenesis kit according to the manufacturer's instructions (Life Technologies, Grand Island, N.Y.). Briefly, human umbilical vein endothelial cells (HUVECs) were established at $2 \times 10^5$ cells per T-75 flask using 200PRF medium containing a low serum growth supplement [i.e. 2% (v/v) FBS and bFGF (3 ng/mL)]. Medium was changed every other day until cultures were approximately 80% confluent. HUVEC cells were trypsinized and washed with non-supplemented 200PRF medium.

HUVEC cells were then suspended with one of three selected medium to achieve a plating concentration of $4.0 \times 10^4$ cells/cm$^2$. The three different medium included LSGS-supplemented medium 200PRF (positive inducer control), LSGS-supplemented medium containing 30 µM suramin (positive inhibitor control) or AF. After suspending HUVECs (8000 viable cells/cm$^2$) in each of the different selected medium, cells were seeded in 24-well plates pre-coated with Geltrix™. To pre-coat plates, Geltrex™ (50-100 µL) was added to each well of a 24-well plate and incubated for 30 min at 37° C. to allow the gel to solidify. The HUVECs were incubated at 37° C., 5% $CO_2$ for 3 h. Each well was scored from a 0-4+ for tubule formation relative to the amount of tube formation in the positive control.

Protein Arrays

AF (1 mL) from three maternal collections were sent to a contract testing facility for quantitative screening using the Quantibody® Human Cytokine Antibody Array 9000. This array set consists of nine glass chips that simultaneously and quantitatively measure the concentration of 400 human cytokines. Controls and serial dilutions of cytokine standards were prepared according to the manufacturer's instructions. Chips were blocked with 100 μL of Sample Diluent at room temperature for 30 min. After decanting the diluent from each chip, cytokine standards, controls and test samples were added to chip wells and were incubated at room temperature for 1-2 h. Each chip was washed three times and then incubated for 1 h at room temperature in the dark with a Cy3 equivalent dye-streptavidin conjugate. The dye was decanted and chips were washed five times with a 1× wash buffer at room temperature, dried and imaged using a laser scanner equipped with a Cy3 wavelength. Quantitative data analysis was performed using the Quantibody® Q-Analyzer software. Positive controls in each array were used for normalization. Classification of proteins according to biological function was obtained by surveying various databases and literature sources. Cluster Analysis was performed using the free software program from The R Project for Statistical Computing.

Epidermal Growth Factor (EGF) ELISA

Quantitative sandwich enzyme-linked immunosorbent assays (Elisa) were conducted according to the manufacturer's instructions (R&D, Systems, Inc, Minneapolis, Minn.). Briefly, duplicate standards and duplicate test samples of AF were tested in different wells of a microplate pre-coated with monoclonal antibody specific for EGF. After incubating the plate at room temperature for 2 h, unbound substance was washed away and an enzyme-linked polyclonal antibody specific for EGF was added to the wells. The plate was incubated at room temperature for 1 h. After washing, substrate solution was added to each well, incubated for 20 min in the dark followed by the addition of a stop solution. The optical density of each well was read at 540 nm using a microplate reader and the concentrations of the samples were determined using the standard curve. Criteria for intra- and inter-assay variations were a coefficient of variation of ≤10%.

Statistical Analysis

Data are presented as mean±standard deviation from the mean and in some cases a median is provided. A student t test was used to determine differences or similarities between populations. P values <0.05 were designated as significant.

Results

Amniotic Fluid (AF) Collection

AF was successfully collected from 17 donors. AF was immediately transported to the testing facility and was processed within 24 h of collection. Upon arrival of the AF at the testing facility and prior to processing, each AF collection was evaluated for total volume and appearance. AF collections with meconium and/or excessive blood contamination were not processed.

Pre-Processing Characterization of Amniotic Fluid

The average total volume of AF collected was 152±230 mL (n=17; mean±SD) with a median collection volume of 70 mL and a range of 10-815 mL. However, this high variability was largely due to the difference in experience and training between the various medical personnel performing the collections.

When visibly contaminated with blood, the color of AF went from red to pink. When no blood contamination was evident, the color of the AF ranged from colorless to dark yellow. Turbidity scores of 1+ to 4+ were assigned to each AF, where zero equals no turbidity and 4+ equals a flocculent appearance. A majority of pre-processed AF collections scored a 4+. No samples received turbidity scores of 2+ or 0.

Randomly selected AFs were evaluated for fluid chemistries. Before processing the AF, average total protein levels were 3.3±0.2 mg/mL with a median value of 3.3 mg/mL (n=3) Average electrolyte, sodium, potassium, chloride, carbon dioxide, urea nitrogen, creatinine, and glucose levels are shown in Table 1 (n=6). HA levels in AF averaged 311±75 ng/mL with a median of 313 ng/mL and a range of 198-416 ng/mL (n=8).

TABLE 1

| Electrolyte | Mean ± SD | Median |
|---|---|---|
| Sodium (mmol/L) | 122 ± 7 | 125 |
| Potassium (mmol/L) | 4.2 ± 0.4 | 4.3 |
| Chloride (mmol/L) | 98 ± 5 | 101 |
| Urea nitrogen (mg/dL) | 18 ± 5 | 17 |
| Creatine (mg/dL) | 2.2 ± 0.4 | 2.1 |
| Glucose (mg/dL) | 10 ± 8 | 8 |
| Calcium (mg/dL) | 6.4 ± 0.8 | 6.3 |

Post-Processing Characterization of Amniotic Fluid Supernatant

AF was processed by first centrifuging and then filtering the fluid to remove particulates (i.e. lanugo, vernix and cells). After centrifugation, the supernatant was removed from the cell pellet and the supernatant was sequentially filtered to obtain a sterile filtered fluid with volume recoveries of 71±23% (n=11). Turbidity scores of the AF decreased from an average pre-filtration score of 2.6+ to a post-filtration score of 1+. Post-processing recoveries for HA were 99.8±4.2%. Post processing recovery levels for sodium, potassium, chloride, carbon dioxide, anion gap, urea nitrogen, creatinine and glucose were all >90% (FIG. 1). Overall, processing of AF resulted in an average decrease in total protein levels from 3.3±0.2 to 2.8±0.3 mg/mL (mean±SD; n=3) with a recovery of 84.4±12.8% of the total protein. EGF pre-filtration levels for AF averaged 204.2±80.6 ng/mL and after filtration EGF levels averaged 203.9±100.7 ng/mL for overall recovery levels of 95.2±16.4%, Post-processing sterility test results for aerobic, anaerobic and fungal microorganisms were negative for six of six randomly selected AFs.

Therefore, these results show that electrolytes, creatinine, urea nitrogen, glucose and total protein levels are similar among donors. However, HA levels did vary among full-term pregnancy donors (median 313 ng/mL; range 198-416). Further, the sterile filtration process used in this study did result in a retention of HA, electrolytes, creatinine, urea nitrogen, and glucose levels, but total protein levels decreased by approximately 26% in the AFs. The decline in protein levels during the filtration process may be attributable to the removal of proteins embedded in vernix as it is caught in the filters. Exactly which proteins are the most affected by the filtration process are not yet known. However, it is noted that despite the decrease in overall protein levels, EGF levels remained unaffected by filtration.

The angiogenic activity of AF was measured using an in vitro endothelial tube formation assay. Three different AFs were randomly selected for testing to determine whether pre- and post-filtered AF supported endothelial tube formation. Representative figures of endothelial tube formation for negative and positive controls as well as for pre- and post-filtered AF are shown in FIGS. 2A-2H. Further, the results illustrated in Table 2 show that endothelial tube formation was supported independent of whether AF was filtered or not. Also, endothelial tube formation was observed to be similar for each of three different AFs that were tested.

TABLE 2

| Lot Identification | | Qualitative Functional Assessment | |
|---|---|---|---|
| | | 2-hour | 4-hour |
| AF Sample 1 | Pre-Filter | + | ++ |
| | Post Filtration | + | ++ |
| AF Sample 2 | Pre-Filter | + | ++ |
| | Post Filtration | + | ++ |
| AF Sample 3 | Pre-Filter | + | ++ |
| | Post Filtration | + | ++ |
| POSITIVE INDUCTION | | +++ | ++++ |
| INDUCTION INHIBITION | | − | − |

AF = Amniotic Fluid

Cytokine Profile of AF

Cytokine antibody arrays were used to simultaneously identify and quantitate protein levels for 400 human cytokines from three randomly selected AF donors. Prior to performing the arrays, each of three lots of AF underwent a sterile filtration process. Protein arrays were performed in replicates of four for each of three lots. Using a mean cut-off of 8±8 pg/mL the total number of proteins present in each of the three lots was 318, 313 and 282 (See FIGS. 3A-3G). This resulted in an average of 304±20 cytokines being detected out of 400 cytokines tested or 72% of the cytokines that were tested showed a positive signal in AF.

Each protein with a positive signal was assigned a biological function based on annotated information obtained from Entrez Gene, GeneCards, UniProtKB/Swiss-Prot, Gene Wiki, and the Human Protein Reference databases. Cytokines were assigned to 12 different functional categories. There were also a handful of proteins that were designated as having poorly described functional activities (i.e. unknown) and some proteins that were designated as miscellaneous because they did not meet the criteria for one of the twelve defined functional categories (i.e.) (FIG. 4A).

Figure 4A:
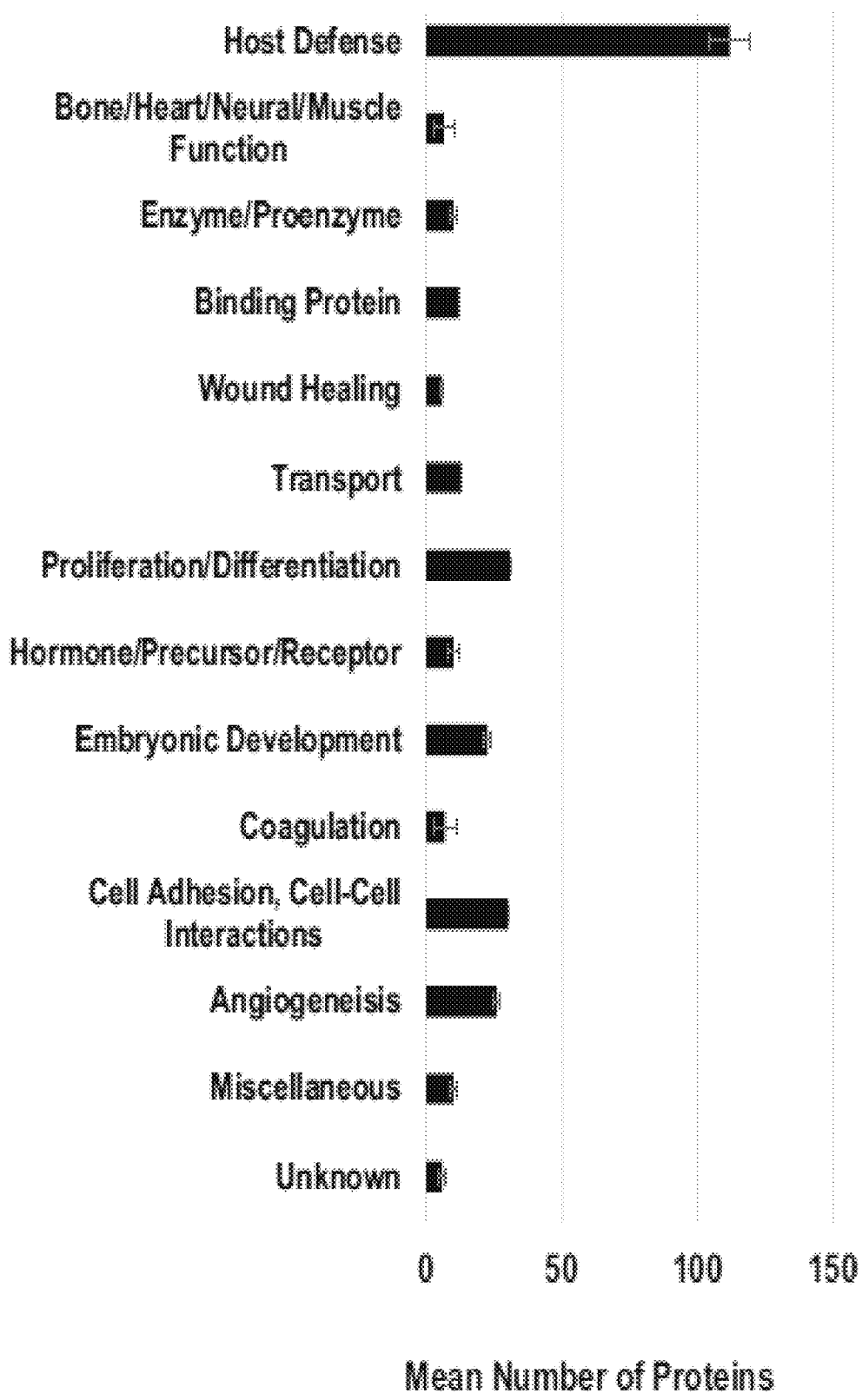
FIG. 4A depicts a chart classifying various proteins found in amniotic fluid samples according to biological function. Biological functions were assigned based on information queried from Entrez Gene, GeneCards, UniProtKB/Swiss-Prot, Gene Wiki, and the Human Protein Reference databases. Each of the proteins were matched to 12 defined biologically functional groups. Proteins with defined functional activities that did not meet any of the 12 functional categories were designated as miscellaneous proteins and proteins with no known functional activity were designated as unknown.
Figure 4B:
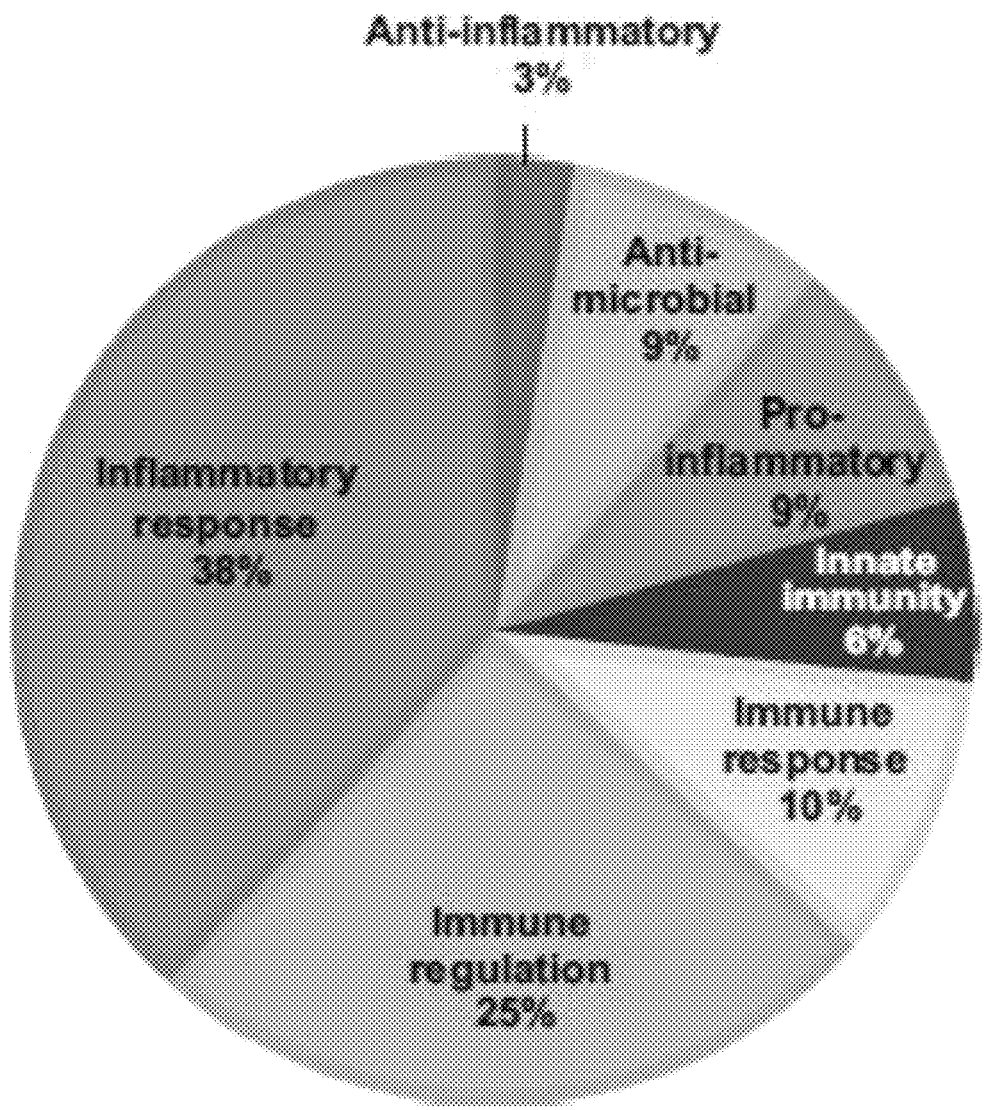
FIG. 4B depicts a chart further categorizing proteins classified as having involvement in host defense into sub-categories of proteins with inflammatory activity, anti-microbial activity, involvement in the immune response, and immune regulation.

A majority of cytokines (i.e. 39%) were categorized as participating in host defense (FIG. 4A). The host defense proteins were further sub-categorized and found to have known functions associated with the inflammatory response, innate immunity or as an antimicrobial (FIG. 4B). The next biggest categories of similar functioning proteins were for proteins involved in cell adhesion, proliferation and angiogeniesis (FIG. 4A). Proteins that were classified as having poorly defined functional activities included serum amyloid A (SAA), cathepsin S (CTSS), Interleukin-36 alpha (IL-36a), mycobacterial porin (MSPa), interferon-alpha/beta receptor beta chain (IFNAR2), and G protein-coupled receptor associated sorting protein (GASP2). Proteins assigned to the miscellaneous category included proteins involved in $Ca^{2+}$ regulation, apopotosis, cell migration, lysosomal sorting and ectodermal organ morphogenesis. More specifically this included the proteins: Procalcitonin, two death proteins (HTRA2 and TRAIL-R4), ectodysplasin A (EDA-A2), a protease inhibitor, Cystatin C, a nucleosome assembly protein, NAP-2, protein-coupled receptor associated sorting protein (GASP-1), stromal derived factor-1a, (SDF-1a), carbohydrate antigen 19-9 (CA19-9), and agouti-related protein (AgRP).

Figure 5A:
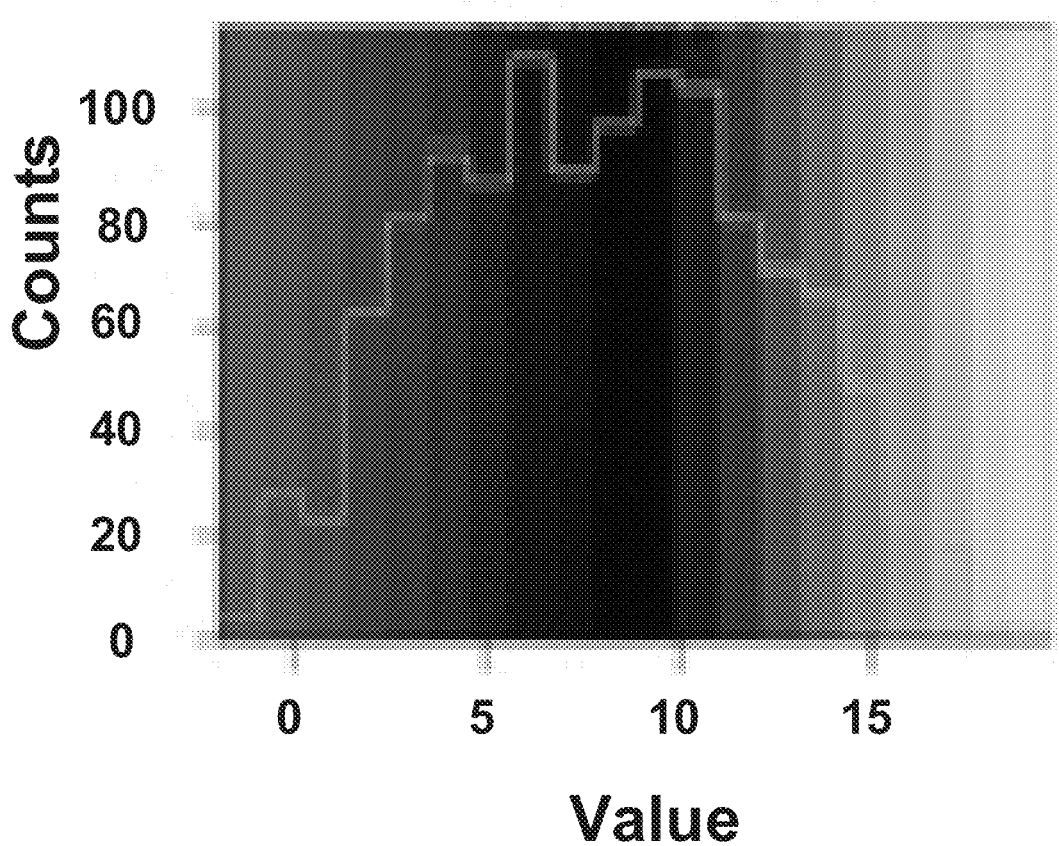
FIG. 5A illustrates a color key and histogram for the hierarchical cluster heat map of FIG. 4B.
Figure 5B:
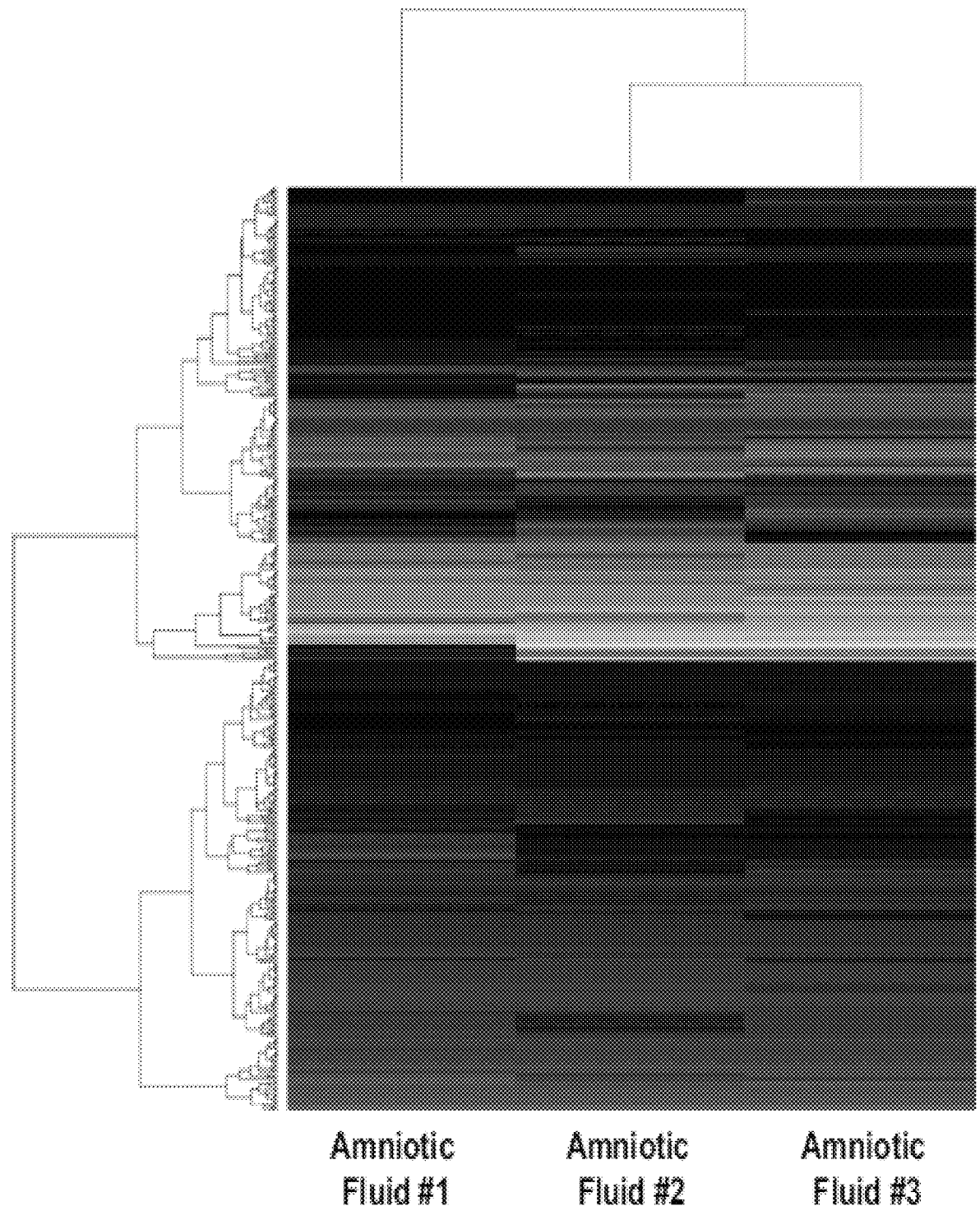
FIG. 5B depicts a hierarchical cluster analysis heat map. Cluster analysis was performed after removing proteins that showed no detectable signal from all three AF samples. Low expression protein values are represented as grey, high expression protein values are represented as white, and intermediate values are black.

Approximately 90% of the proteins that were detected in AF were present in all 3 AF samples. The remaining 10% of proteins were found in either one or two of the AF samples, but not in all three lots. Variances in expression levels for proteins present in all three collections were identified using the criteria that a ≥1.5-fold increase or ≤0.65-fold decrease in signal intensity between protein levels was a measurable and significant difference among analytes. Using these criteria, no measurable differences in expression levels were observed for 53.5±4.2% of the cytokines, whereas, 47.5±2.8% of the cytokines were noted to have measurable differences in expression levels. Differences in protein expression levels among three lots of AF were best illustrated by the proteins, periostin, and PDGFRα, which were the two most highly expressed proteins in two of the three AF tested. Periostin levels in these two AF collections were 6.3 and 1.1 µg/mL, but in the third AF was only 3.7 pg/mL. PDGFRα levels were 2.5 and 5.7 µg/mL in two of the AF collections, but were undetectable in the third fluid. An overall manual inspection of the data suggested that two of the AFs were more alike to one another than the third AF. This observation was confirmed using a statistical and graphical program to perform hierarchical cluster analysis. After removing proteins that had no signal, cluster analysis of the data confirmed that samples #2 and #3 were more alike one another than to sample #1 (FIGS. 5A-5B).

Therefore, protein arrays of post-filtered AFs show that the fluid remains rich in cytokines with antimicrobial, immunomodulatory, and growth-promoting activities. Given that AF functions as a supportive cushion to the fetus and provides a protective environment, it is interesting that a majority of proteins fell into the category of host defense. The host defense proteins identified by this study add to an arsenal of bioactive molecules that are already known to be present in AF (i.e. lysozyme, peroxidase, transferrin, β-lysin, immunoglobulins and zinc-peptide complexes) to combat an invasion of microorganisms during the gestational period. Additionally, proteins for angiogenesis were identified with the protein arrays and this study shows that AF is angiogenic as illustrated by the endothelial tube formation assay.

Thus, even though there is donor variability in both cytokine levels and composition, the arrays show that a large majority of the same cytokines are present in AFs collected from different donors. However, the cytokine arrays show that the profiles of two of the three AFs are more similar to one another than to a third fluid (FIGS. 5A-5B). An examination of maternal donor charts to determine whether there is any obvious differences between the two similar samples and the third sample, did not reveal any significant maternal donor variables that might account for protein profile differences/similarities based on factors such as the gestational age of the fetus, the reason for C-section, or maternal history. Given the complexity and changes in the regulatory pathways utilized during pregnancy that define the composition of AF, it is not surprising that donor variability is observed among AF collections.

Characterization of the AF Cell Pellet

Figure 6:
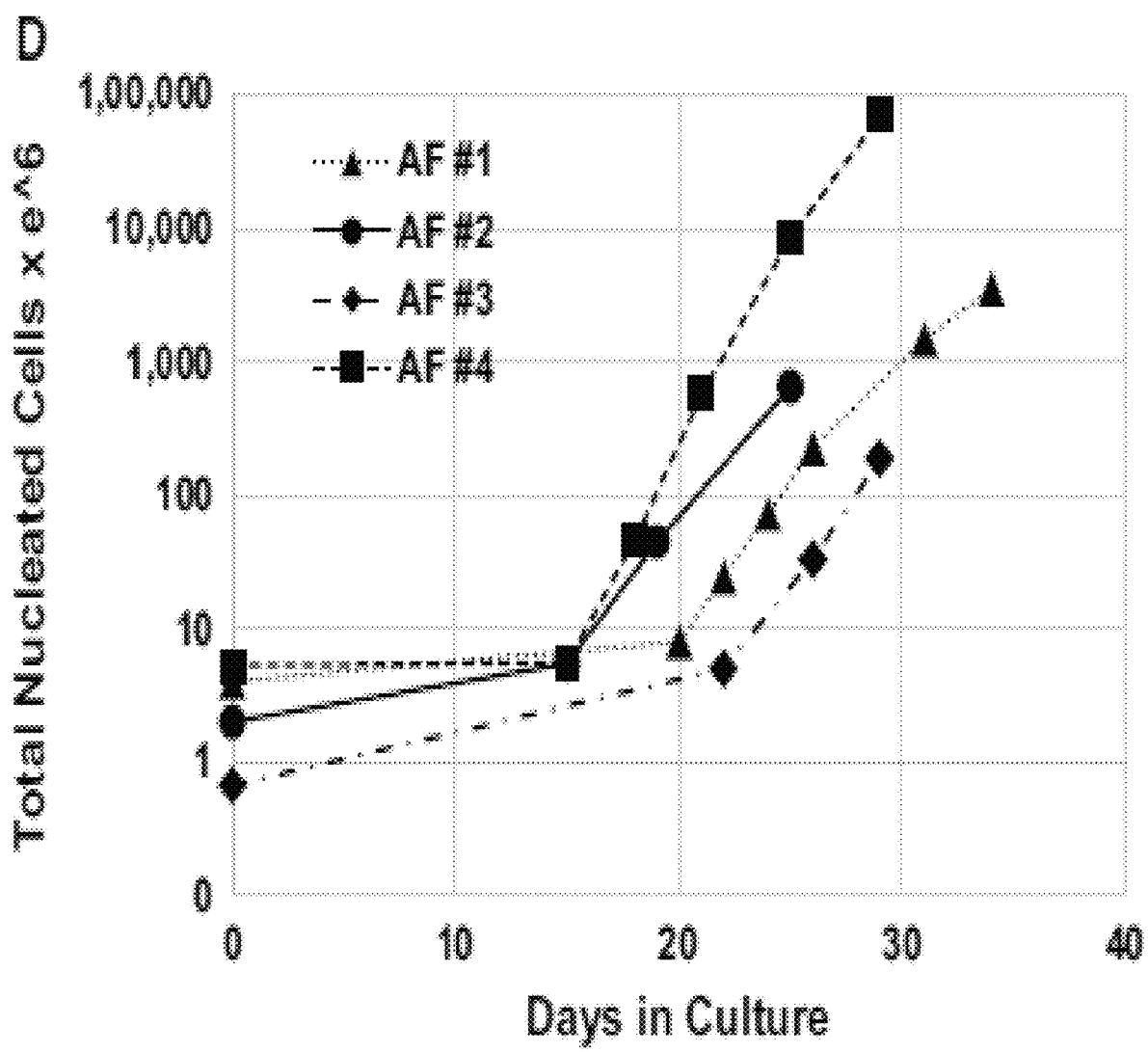
FIG. 6 depicts a graph illustrating the proliferative response of adherent cells present in pre-processed AF. The AF cells were cultured over multiple passages for the designated time periods. Each symbol except for time zero point represents when a passage was performed for a given culture.

Microscopic examination of cell pellets obtained after centrifugation of AF from four randomly selected donors revealed that a majority of cells were epitheloid cells with the bulk of these cells being non-viable. Among the non-viable epitheloid cells was a minor population of lymphoid cells that were present at an average concentration of 6045±780 cells per mL of fluid (n=4). When cell pellets from AF were plated using an adherent cell culturing strategy, an average of 39±17 adherent focal colonies were formed at approximately 2-3 weeks of culture. The focal colonies exhibited extensive proliferation potential with subsequent passages (FIG. 6). AF #1, AF #2, AF #3 and AF #4 underwent 6, 3, 3 and 5 passages, respectively. The immunophenotype of the expanded cells expressed cell surface antigens associated with MSCs, (Table 3) and cells differentiated into adipocytes, osteocytes and chondrocytes.

Thus, this study shows that a majority of nucleated cells found in AF are non-viable squamous epithelial cells. Among these cells is a minor population of cells with a high proliferative potential that can be isolated and expanded using an adherent cell culture strategy. The resulting cells display an MSC immunophenotype and have tri-lineage potential. This is consistent with observations that a highly proliferative population of a rare population of stromal cells is present in AF. Due to a rarity of viable precursor MSCs in AF, it is unlikely in a clinical setting that non-expanded cells from small volumes of AF (i.e. 1-2 mL) will contribute significantly to reparative and regenerative processes.

TABLE 3

| Antigen | Percent positive | | | |
|---|---|---|---|---|
| | AF#1 | AF#2 | AF#3 | AF#4 |
| CD90+ | 94.7 | 98.1 | 75.2 | 98.8 |
| CD73+ | 98.4 | 99.6 | 98.6 | 99.5 |
| CD166+ | 100.0 | 92.3 | 98.6 | 99.6 |
| CD14+ | ND | 0.0 | 0.22 | ND |
| CD34+ | 0.0 | 0.0 | 0.23 | 0.7 |
| CD45+ | 0.0 | 0.0 | 0.40 | ND |
| HLA-DR+ | 0.0 | 0.0 | 0.29 | 0.67 |
| HLA-ABC+ | 100.0 | 99.2 | ND | 99.6 |

AF amniotic fluid

Example 2—Evaluation of Amniotic Fluid at Different Stages of the Manufacturing Process Amniotic fluid was further evaluated at various stages of the manufacturing process to determine what differences might be present in the freshly harvested amniotic fluid, as compared the centrifuged amniotic fluid and the subsequently filtered amniotic fluid. This was performed by measuring differences in particle counts and optical density at each of the identified stages of the manufacturing process.

The sizing and particulate testing was performed using the HIAC Royco Liquid Particle Counting System (LPC). The counter detects and sizes particles using a light-obscuration sensor. A positive control was performed by testing a solution containing latex beads of 10 μm and 25 μm in diameter. Particulate matter is defined in the USP as extraneous, mobile, undissolved substances other than gas bubbles, unintentionally present in or on a solution or device. The results of are illustrated in Table 4 below:

TABLE 4

| Sample | Particles per mL (≥10 μm) | Particles per mL (≥25 μm) |
|---|---|---|
| Pre-Processed | 26,540 | 770 |
| Centrifuged | 13,594 | 333 |
| Final Product | 189 | 7 |

Figure 7:
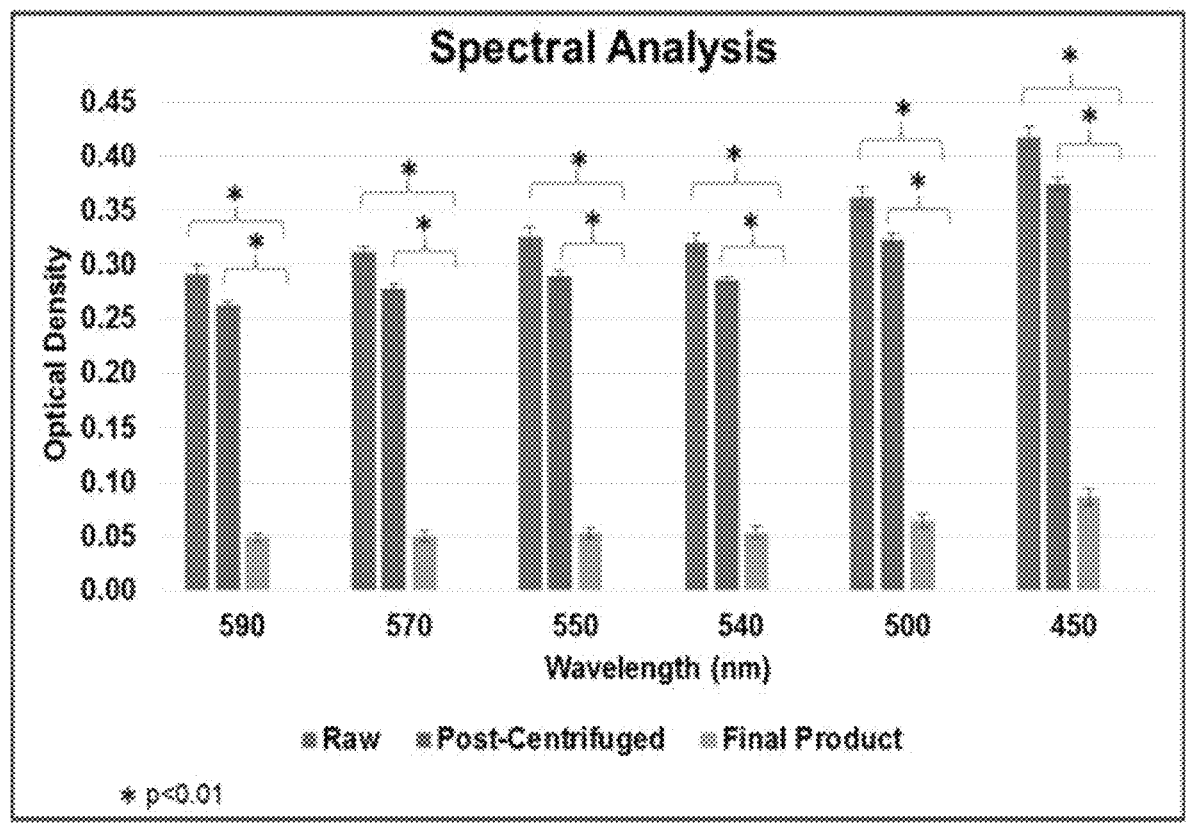
FIG. 7 depicts a chart illustrating optical density measurements for AF samples at various stages of the manufacturing process. At each wavelength, pre-processed, centrifuged, and final product values are listed sequentially from left to right.

Spectral analysis was conducted by determining the optical density of the aliquots that were collected from pre-processed, centrifuged, and final products of amniotic fluid. Five-100 ml aliquots from the pre-processed, centrifuged, and final product samples were pipetted into 5 wells of a 96 well flat bottom plate (i.e. 5 replicates). The absorbance of each well at 590 nm, 570 nm, 550 nm, 540 nm, 500 nm and 400 nm was measured using a Molecular Devices Spectra-Max M2 spectrophotometer. The absorbance of the pre-centrifuged, post-centrifuged, and filtered final product was then compared for significant differences using a standard t-test (See FIG. 7).

Is illustrated in this study, the final products (i.e. centrifuged and filtered AF samples) exhibited significantly reduced particulate counts and optical density as compared to raw harvested amniotic fluid. This is evident by the hazy appearance of the freshly harvested amniotic fluid as compared to the final product. Thus, it is clear that there are compositional differences between the freshly harvested amniotic fluid and the final product that has been both centrifuged and filtered.

Example 3—Amniotic Fluid Treatments

Various patients were treated for different medical conditions including burns and burn scars, chronic wounds, ulcers, a failed urethroplasty, and ocular GvHD in a bone marrow transplant patient. It is noted that in each case the treated patients had some degree of improvement, with some having full wound closure. A few specific examples are provided below for illustrative purposes.

Figure 8A:
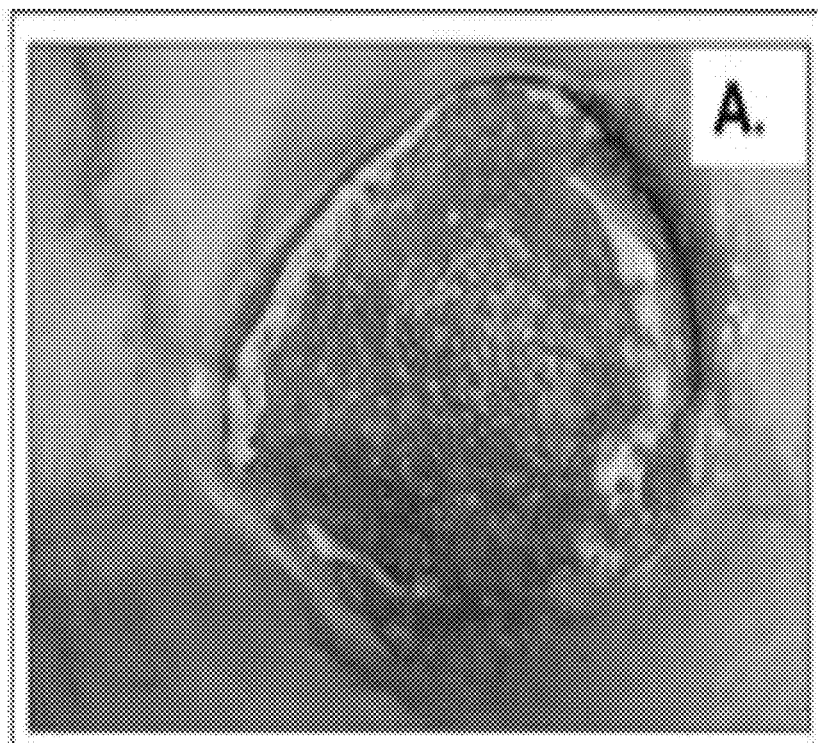
FIG. 8A illustrates a chronic abdominal wound prior to treatment with processed amniotic fluid.
Figure 8B:
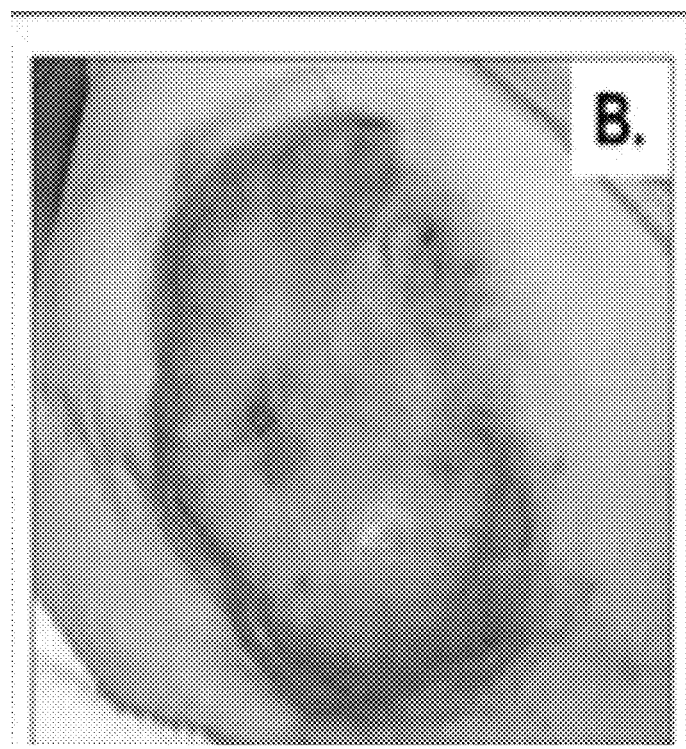
FIG. 8B illustrates the wound of FIG. 8A after treatment with processed amniotic fluid, in accordance with examples of the present disclosure.

Case 1: Amniotic fluid was evaluated in patients with non-healing wounds. In one patient, an abdominal wound was open for over 1 year that was related to 20+ previous abdominal surgeries (See FIG. 8A). Previous failed wound care strategies included repeated wound vacuum treatments and hyperbaric oxygen therapy. The patient also received multiple autologous skin grafts, each of which failed. Persistent and copious purulent drainage of the wound was observed at the time of treatment with AF. Initially, the wound was treated with amnion alone with no observed improvement. This was followed by an application of amnion and misting of AF onto the wound. Approximately, 1 week post treatment there was a noted difference in the wound. Subsequent circumferential injections of AF resulted in decreased wound size and erythema with maturation of a skin graft with 98% graft take. Complete closure of the wound occurred within 4-5 months of treatment with AF (See FIG. 8B).

Figure 9A:
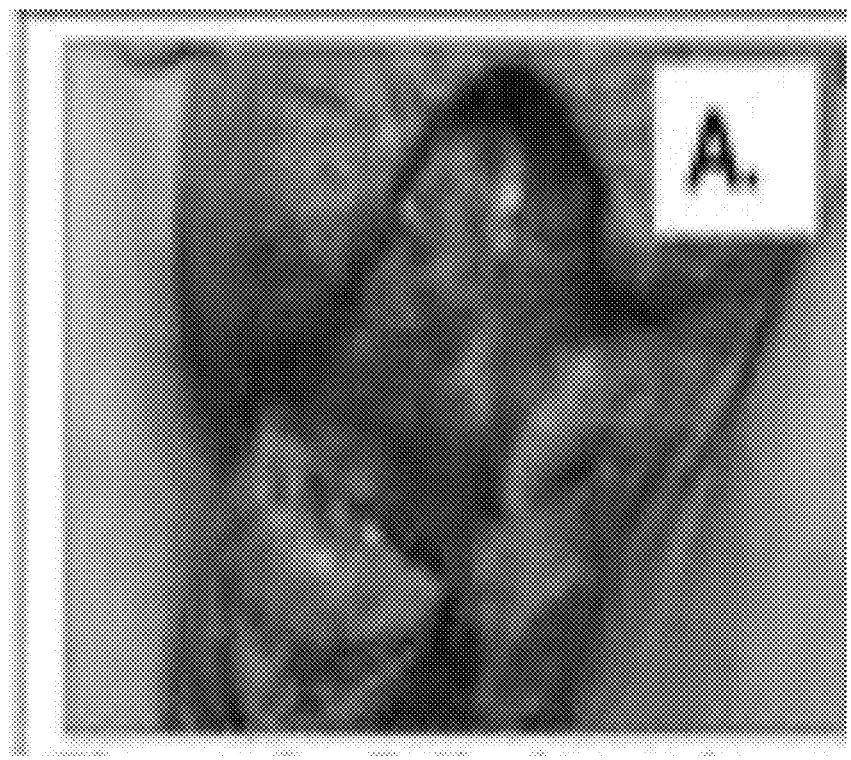
FIG. 9A illustrates a wound site associated with a failed urethroplasty prior treatment with processed amniotic fluid.
Figure 9B:
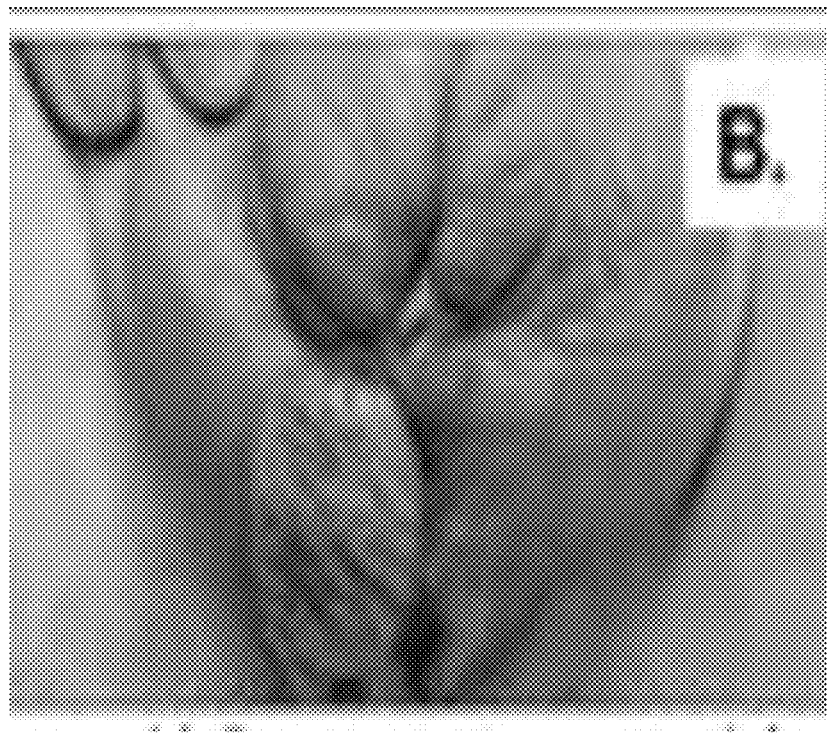
FIG. 9B illustrates the wound site of FIG. 9A after treatment with processed amniotic fluid, in accordance with examples of the present disclosure.

Case 2: Amniotic fluid was evaluated in a patient with a failed urethroplasty and had an open wound for 4+ months (See FIG. 9A). Due to increased risk for bleeding, the open wound was injected with 8-9 mL of AF. Within 2 weeks of the injection of AF there was significant wound closure. The patient was again injected with 8-9 mL AF. After an additional 2 weeks there was almost complete wound closure (See FIG. 9B).

Figure 10A:
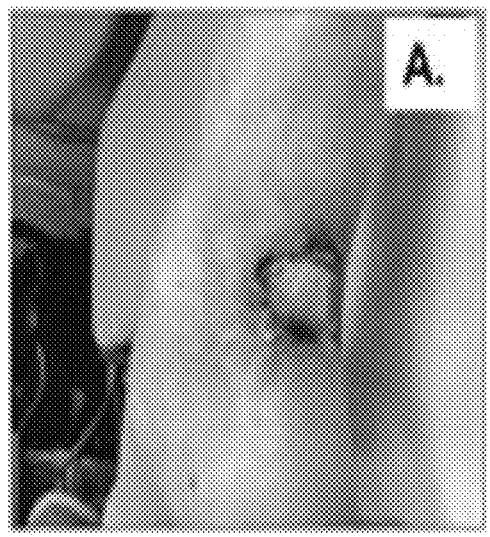
FIG. 10A illustrates a Martorell's ulcer prior to treatment with processed amniotic fluid.
Figure 10B:
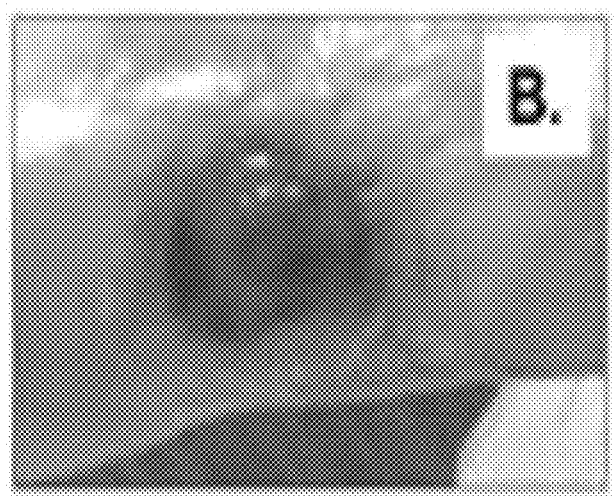
FIG. 10B illustrates the ulcer of FIG. 10A after treatment with processed amniotic fluid over a period of 1 month, in accordance with examples of the present disclosure.
Figure 10C:
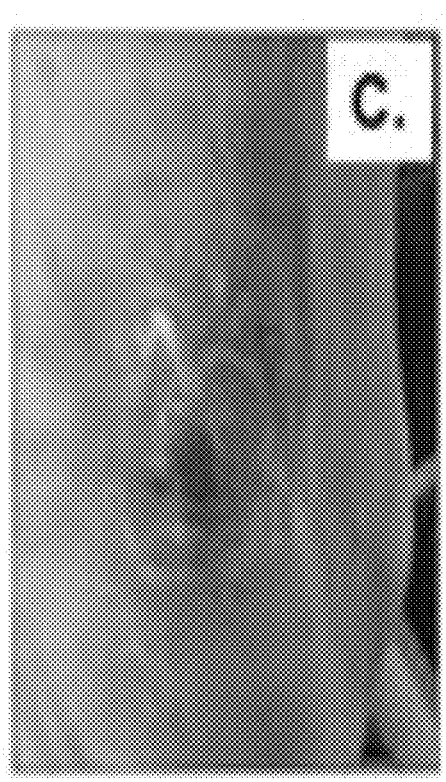
FIG. 10C illustrates the ulcer of FIG. 10B after additional treatment with processed amniotic fluid over a period of an additional month (two months total), in accordance with examples of the present disclosure.

Case 3: Amniotic fluid was evaluated in a patient with a Martorelli's Ulcer for over a year. The non-healing ulceration included an extremely painful lesion with the tendon exposed (See FIG. 10A). Within 1-2 weeks of treatment with about 6 mL of AF, noticeable granulation of the wound was observed (See FIG. 10B). Subsequent treatments of the wound with about 20-30 mL of AF over a 3-4 month period resulted in re-epithelialization and almost complete closure of the wound (See FIG. 10C).

It should be understood that the above-described methods are only illustrative of some embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that variations including, may be made without departing from the principles and concepts set forth herein.

What is claimed is:

1. A therapeutic composition, comprising:
an amount of processed amniotic fluid having a therapeutically effective amount of protein and hyaluronic acid (HA), said composition being substantially free of lanugo, vernix, and cells harvested with amniotic fluid, wherein the protein is present in an amount from about 0.15 mg/ml to about 10 mg/ml and wherein the composition is lyophilized and has an optical density of less than 0.20 when exposed to electromagnetic radiation at a wavelength of 590 nm in a liquid form.

2. The composition of claim 1, wherein the composition has less than or equal to 10,000 particles per milliliter of particles having a particle size of 10 microns or greater.

3. The composition of claim 1, wherein the composition has less than or equal to 300 particles per milliliter of particles having a particle size of 25 microns or greater.

4. The composition of claim 1, further comprising hemoglobin in an amount from 1 µg/ml to 60 µg/ml.

5. The composition of claim 1, further comprising an active agent.

6. The composition of claim 5, wherein the active agent is a member of the group consisting of an anti-infective agent, an antibiotic, an anti-tumor agent, an anti-inflammatory agent, a pain-controlling agent, an anti-rheumatic agent, a bisphosphonate, a supplementary growth factor, a supplementary cytokine, an amino acid, a protein, a vaccine, a hormone, a vitamin, a phytoestrogen, fluoride, and combinations thereof.

7. The composition of claim 1, further comprising a pharmaceutically acceptable carrier.

8. The composition of claim 7, wherein the pharmaceutically acceptable carrier is formulated for administration via injection, enteral administration, topical administration, transdermal administration, transmucosal administration, inhalation, or implantation.

9. The composition of claim 7, wherein the therapeutic composition is formulated as a bone graft material.

10. The composition of claim 7, wherein the therapeutic composition is formulated as a biocompatible injectable adhesive.

11. A therapeutic composition, comprising:
an amount of processed amniotic fluid; and
a therapeutically effective amount of protein and hyaluronic acid, wherein the protein is present in an amount of from about 0.15 mg/ml to about 10 mg/ml, wherein the composition is substantially free of lanugo, vernix, and cells harvested with amniotic fluid; and
wherein the composition is lyophilized and has an optical density of less than 0.20 when exposed to electromagnetic radiation at a wavelength of 590 nm in a liquid form.

12. The composition of claim 11, wherein the composition has less than or equal to 10,000 particles per milliliter of particles having a particle size of 10 microns or greater.

13. The composition of claim 11, wherein the composition has less than or equal to 300 particles per milliliter of particles having a particle size of 25 microns or greater.

14. The composition of claim 11, further comprising hemoglobin in an amount from 1 µg/ml to 60 µg/ml.

15. The composition of claim 11, further comprising an active agent.

16. The composition of claim 15, wherein the active agent is a member of the group consisting of an anti-infective agent, an antibiotic, an anti-tumor agent, an anti-inflammatory agent, a pain-controlling agent, an anti-rheumatic agent, a bisphosphonate, a supplementary growth factor, a supplementary cytokine, an amino acid, a protein, a vaccine, a hormone, a vitamin, a phytoestrogen, fluoride, and combinations thereof.

17. The composition of claim 11, further comprising a pharmaceutically acceptable carrier.

18. The composition of claim 17, wherein the pharmaceutically acceptable carrier is formulated for administration via injection, enteral administration, topical administration, transdermal administration, transmucosal administration, inhalation, or implantation.

19. A method of manufacturing a therapeutic processed amniotic fluid composition, comprising:
harvesting amniotic fluid from a pregnant female to provide a harvested amniotic fluid, said harvested amniotic fluid having a therapeutically effective amount of protein and hyaluronic acid HA, wherein the protein is present in an amount of from about 0.15 mg/ml to about 10 mg/ml,
centrifuging the harvested amniotic fluid to form supernatant and a cell pellet;
filtering a portion of the supernatant to prepare a therapeutic amniotic fluid composition that is substantially devoid of lanugo, vernix, and cells; and
lyophilizing the composition;
wherein the composition has an optical density of less than 0.20 when exposed to electromagnetic radiation at a wavelength of 590 nm in a liquid form.

20. The method of claim 19, wherein the therapeutic amniotic fluid has 60% or more of the therapeutic protein content of the extracted amniotic fluid.

21. The method of claim 19, wherein the therapeutic amniotic fluid has 80% or more of the hyaluronic acid content of the extracted amniotic fluid.

22. The method of claim 19, wherein extracting comprises:
performing an abdominal fenistil incision through the abdominal and uterine muscles of the pregnant female without cutting into the amnion membrane;
inserting a suction catheter into the amnion membrane, said suction catheter being fluidly connected to a suction container; and
suctioning amniotic fluid into the suction container.

23. The method of claim 19, wherein centrifugation is performed at a relative centrifugal force of from 1000×g to 1800×g.

24. The method of claim 19, wherein filtering comprises:
passing supernatant through a first filter to prepare a filtered supernatant; and
passing the filtered supernatant through a second filter to prepare the therapeutic amniotic fluid composition.

25. The method of claim 24, wherein the first filter has a pore size of from 40 µm to 70 µm.

26. The method of claim 24, wherein the second filter has a pore size of from 0.1 μm to 0.2 μm.

27. The method of claim 24, wherein the first filter and the second filter are loaded into a common housing.

28. The method of claim 24, wherein the first filter and the second filter are loaded into independent housings that are fluidly connected.

* * * * *